(12) United States Patent
Kopka et al.

(10) Patent No.: US 10,016,519 B2
(45) Date of Patent: Jul. 10, 2018

(54) 18F-TAGGED INHIBITORS OF PROSTATE SPECIFIC MEMBRANE ANTIGEN (PSMA), THEIR USE AS IMAGING AGENTS AND PHARMACEUTICAL AGENTS FOR THE TREATMENT OF PROSTATE CANCER

(71) Applicants: DEUTSCHES KREBSFORSCHUNGSZENTRUM, Heidelberg (DE); RUPRECHT-KARLS-UNIVERSITÄT HEIDELBERG, Heidelberg (DE)

(72) Inventors: Klaus Kopka, Dossenheim (DE); Martina Benesova, Heidelberg (DE); Jens Cardinale, Mannheim (DE); Matthias Eder, Mannheim (DE); Martin Schäfer, Neckarsteinach (DE); Ulrike Bauder-Wüst, Schriesheim (DE); Uwe Haberkorn, Schwetzingen (DE); Michael Eisenhut, Heidelberg (DE)

(73) Assignees: DEUTSCHES KREBSFORSCHUNGSZENTRIUM, Heidelberg (DE); RUPRECHT-KARLS-UNIVERSITÄT HEIDELBERG, Heidelberg (DE)

( * ) Notice: Subject to any disclaimer, the term of this patent is extended or adjusted under 35 U.S.C. 154(b) by 0 days.

(21) Appl. No.: 15/463,059

(22) Filed: Mar. 20, 2017

(65) Prior Publication Data

US 2017/0246327 A1   Aug. 31, 2017

Related U.S. Application Data

(63) Continuation-in-part of application No. PCT/EP2015/001929, filed on Sep. 30, 2015.

(30) Foreign Application Priority Data

Oct. 20, 2014 (EP) ..................... 14003570
Apr. 22, 2015 (EP) ..................... 15164656

(51) Int. Cl.
*A61K 31/04* (2006.01)
*C07B 59/00* (2006.01)
*C07C 275/16* (2006.01)
*C07D 213/82* (2006.01)
*A61K 51/04* (2006.01)

(52) U.S. Cl.
CPC ...... *A61K 51/0455* (2013.01); *A61K 51/0402* (2013.01); *C07B 59/001* (2013.01); *C07B 59/002* (2013.01); *C07C 275/16* (2013.01); *C07D 213/82* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 8,778,305 | B2 | 7/2014 | Pomper et al. |
| 8,926,944 | B2 | 1/2015 | Babich et al. |
| 9,226,981 | B2 | 1/2016 | Pomper et al. |
| 9,388,144 | B2 | 7/2016 | Babich et al. |
| 2011/0142760 | A1 | 6/2011 | Pomper et al. |
| 2013/0034494 | A1 | 2/2013 | Babich et al. |
| 2013/0315821 | A1 | 11/2013 | D'Souza et al. |
| 2014/0369931 | A1 | 12/2014 | Pomper et al. |
| 2015/0078998 | A1 | 3/2015 | Babich et al. |
| 2016/0114060 | A1 | 4/2016 | Pomper et al. |
| 2016/0304555 | A1 | 10/2016 | Wang et al. |

FOREIGN PATENT DOCUMENTS

| | | |
|---|---|---|
| WO | 2010/014933 | 2/2010 |
| WO | 2013/022797 | 2/2013 |
| WO | 2013/028664 | 2/2013 |

OTHER PUBLICATIONS

International Search Report and Written Opinion of the International Searching Authority dated Dec. 18, 2015, which issued during prosecution of International Application No. PCT/EP2015/001929.

*Primary Examiner* — Alicia L Otton
(74) *Attorney, Agent, or Firm* — Vedder Price P.C.; Alain Villeneuve

(57) ABSTRACT

The present invention generally relates to the field of radiopharmaceuticals and their use in nuclear medicine as tracers, imaging agents and for the treatment of various disease states of prostate cancer.

18 Claims, 10 Drawing Sheets

New $^{18}$F-prosthethic groups for peptides a) [$^{18}$F]Fluoroalkynes for "click-chemistry" to triazoles Marik and Sutcliffe Tetrahedron Lett., 2006, 47, 6681.

b) [$^{18}$F]Fluorobenzaldehydes for oxime formation

Poethko et al. J. Nucl. Med., 2004, 45, 892.

Schirrmacher et al. Angew. Chem. Int. Ed., 2006, 45, 6047.

Stochiometric leverage of molar activity in n.c.a. formation of [$^{18}$F]aryltrifluoroboronates

Two step synthesis of azido-rhodamine-[$^{18}$F]trifluoroboronate

Molar activity [Ci/µmol]

|        | $^{18}$F$^-$ (BOS) | [$^{18}$F]product |
|--------|--------------------|-------------------|
| n.c.a. | 6.5                | 15 ± 0.5          |
| c.a.   | 2.7                | 7.7 ± 0.3         |

Z. Lin et al., Angew. Chem. 125, 2359 - 2362 (2013)

Self-immolating fluorescent fluoride sensor assay

S. Y. Kim and J. I. Hong, 9, 3109-3112 (2007)

0 – 20 min p.i.   20 – 40 min p.i.   40 – 60 min p.i.   120 – 140 min p.i.

18F-TAGGED INHIBITORS OF PROSTATE SPECIFIC MEMBRANE ANTIGEN (PSMA), THEIR USE AS IMAGING AGENTS AND PHARMACEUTICAL AGENTS FOR THE TREATMENT OF PROSTATE CANCER

RELATED APPLICATIONS AND INCORPORATION BY REFERENCE

This application is a Continuation-In-Part Application of International Patent Application Serial No. PCT/EP2015/001929 filed Sep. 30, 2015, which published as PCT Publication No. WO 2016/062370 on Apr. 28, 2016, which claims benefit of European Patent Application Serial Nos. 14003570.0 filed Oct. 20, 2014 and 15164656.9 filed Apr. 22, 2015.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention generally relates to the field of radiopharmaceuticals and their use in nuclear medicine as tracers, imaging agents and for the treatment of various disease states of prostate cancer.

BACKGROUND OF THE INVENTION

Prostate cancer (PCa) is the leading cancer in the US and European population. At least 1-2 million men in the western hemisphere suffer from prostate cancer and it is estimated that the disease will strike one in six men between the ages of 55 and 85. There are more than 300,000 new cases of prostate cancer diagnosed each year in the USA. The mortality from the disease is second only to lung cancer. Currently anatomic methods, such as computed tomography (CT), magnetic resonance (MR) imaging and ultrasound, predominate for clinical imaging of prostate cancer. An estimated $2 billion is currently spent worldwide on surgical, radiation, drug therapy and minimally invasive treatments. However, there is presently no effective therapy for relapsing, metastatic, androgen-independent prostate cancer.

A variety of experimental low molecular weight PCa imaging agents are currently being pursued clinically, including radiolabeled choline analogs [$^{18}$F]fluorodihydrotestosterone ([$^{18}$F]FDHT), anti-1-amino-3-[$^{18}$F]fluoro-cyclobutyl-1-carboxylic acid (anti[$^{18}$F]F-FACBC, [$^{11}$C]acetate and 1-(2-deoxy-2-[$^{18}$F]flouro-L-arabinofuranosyl)-5-methyluracil ([$^{18}$F]FMAU) (Scher, B.; et al. *Eur J Nucl Med Mol Imaging* 2007, 34, 45-53; Rinnab, L.; et al. *BJU Int* 2007, 100, 786,793; Reske, S. N.; et al. J Nucl Med 2006, 47, 1249-1254; Zophel, K.; Kotzerke, J. *Eur J Nucl Med Mol Imaging* 2004, 31, 756-759; Vees, H.; et al. *BJU Int* 2007, 99, 1415-1420; Larson, S. M.; et al. *J Nucl Med* 2004, 45, 366-373; Schuster, D. M.; et al. *J Nucl Med* 2007, 48, 56-63; Tehrani, O. S.; et al. *J Nucl Med* 2007, 48, 1436-1441). Each operates by a different mechanism and has certain advantages, e.g., low urinary excretion for [$^{11}$C]choline, and disadvantages, such as the short physical half-life of positron-emitting radionuclides.

It is well known that tumors may express unique proteins associated with their malignant phenotype or may overexpress normal constituent proteins in greater number than normal cells. The expression of distinct proteins on the surface of tumor cells offers the opportunity to diagnose and characterize disease by probing the phenotypic identity and biochemical composition and activity of the tumor. Radioactive molecules that selectively bind to specific tumor cell surface proteins provide an attractive route for imaging and treating tumors under non-invasive conditions. A promising new series of low molecular weight imaging agents targets the prostate-specific membrane antigen (PSMA) (Mease R. C. et al. Clin Cancer Res. 2008, 14, 3036-3043; Foss, C. A.; et al. *Clin Cancer Res* 2005, 11, 4022-4028; Pomper, M. G.; et al. Mol Imaging 2002, 1, 96-101; Zhou, J.; et al. *Nat Rev Drug Discov* 2005, 4, 1015-1026; WO 2013/022797).

PSMA is a trans-membrane, 750 amino acid type II glycoprotein that has abundant and restricted expression on the surface of PCa, particularly in androgen-independent, advanced and metastatic disease (Schulke, N.; et al. Proc Natl Acad Sci USA 2003, 100, 12590-12595). The latter is important since almost all PCa become androgen independent over the time. PSMA possesses the criteria of a promising target for therapy, i.e., abundant and restricted (to prostate) expression at all stages of the disease, presentation at the cell surface but not shed into the circulation and association with enzymatic or signaling activity (Schulke, N.; et al. Proc. Natl. Acad. Sci. USA 2003, 100, 12590-12595). The PSMA gene is located on the short arm of chromosome 11 and functions both as a folate hydrolase and neuropeptidase. It has neuropeptidase function that is equivalent to glutamate carboxypeptidase II (GCPII), which is referred to as the "brain PSMA," and may modulate glutamatergic transmission by cleaving N-acetylaspartylglutamate (NAAG) to N-acetylaspartate (NAA) and glutamate (Nan, F.; et al. J Med Chem 2000, 43, 772-774). There are up to $10^6$ PSMA molecules per cancer cell, further suggesting it as an ideal target for imaging and therapy with radionuclide-based techniques (Tasch, J.; et al. *Crit Rev Immunol* 2001, 21, 249-261).

The radio-immunoconjugate of the anti-PSMA monoclonal antibody (mAb) 7E11, known as the PROSTASCINT® scan, is currently being used to diagnose prostate cancer metastasis and recurrence. However, this agent tends to produce images that are challenging to interpret (Lange, P. H. PROSTASCINT scan for staging prostate cancer. *Urology* 2001, 57, 402-406; Haseman, M. K.; et al. *Cancer Biother Radiopharm* 2000, 15, 131-140; Rosenthal, S. A.; et al. *Tech Urol* 2001, 7, 27-37). More recently, monoclonal antibodies have been developed that bind to the extracellular domain of PSMA and have been radiolabeled and shown to accumulate in PSMA-positive prostate tumor models in animals. However, diagnosis and tumor detection using monoclonal antibodies has been limited by the low permeability of the monoclonal antibody in solid tumors.

Citation or identification of any document in this application is not an admission that such document is available as prior art to the present invention.

SUMMARY OF THE INVENTION

The selective targeting of cancer cells with radiopharmaceuticals, either for imaging or therapeutic purposes is challenging. A variety of radionuclides are known to be useful for radio-imaging or cancer radiotherapy, including $^{111}$In, $^{90}$Y, $^{68}$Ga, $^{177}$Lu, $^{99m}$Tc, $^{123}$I and $^{131}$I. Recently it has been shown that some compounds containing a glutamate-urea-glutamate (GUG) or a glutamate-urea-lysine (GUL) recognition element linked to a radionuclide-ligand conjugate exhibit high affinity for PSMA.

New agents that will enable rapid visualization of prostate cancer and specific targeting to allow radiotherapy present are needed.

Thus, the object of the present invention is to develop ligands that interact with PSMA and carry appropriate radionuclides which provide a promising and novel targeting option for the detection, treatment and management of prostate cancer.

The solution of said object is achieved by providing the embodiments characterized in the claims.

The inventors found new compounds which are useful radiopharmaceuticals and their use in nuclear medicine as tracers, imaging agents and for the treatment of various disease states of prostate cancer.

The novel imaging agents with structural modifications in the linker region have improved tumor targeting properties and pharmacokinetics. The pharmacophore presents three carboxylic groups able to interact with the respective side chains of PSMA and an oxygen as part of zinc complexation in the active center. Besides these obligatory interactions, the inventors were able to optimize the lipophilic interactions in the linker region.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
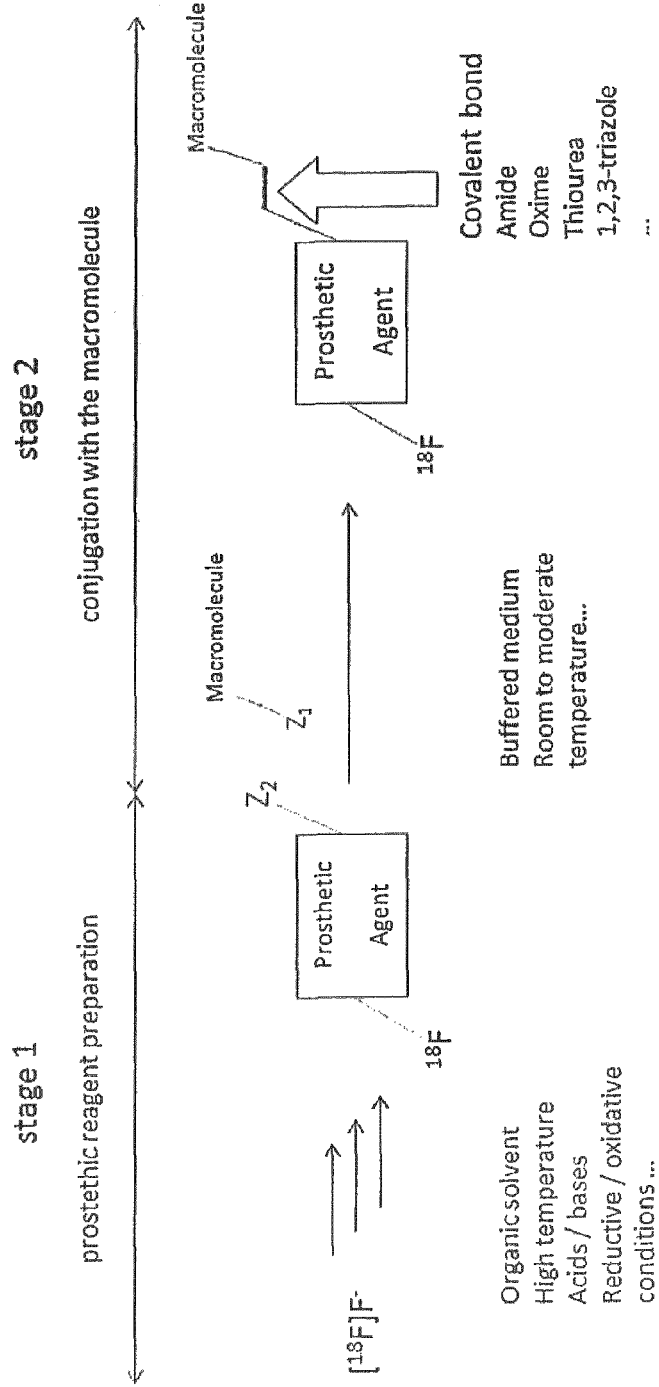
FIG. 1: $^{18}$F-Labelling of macromolecules.
Figure 2:
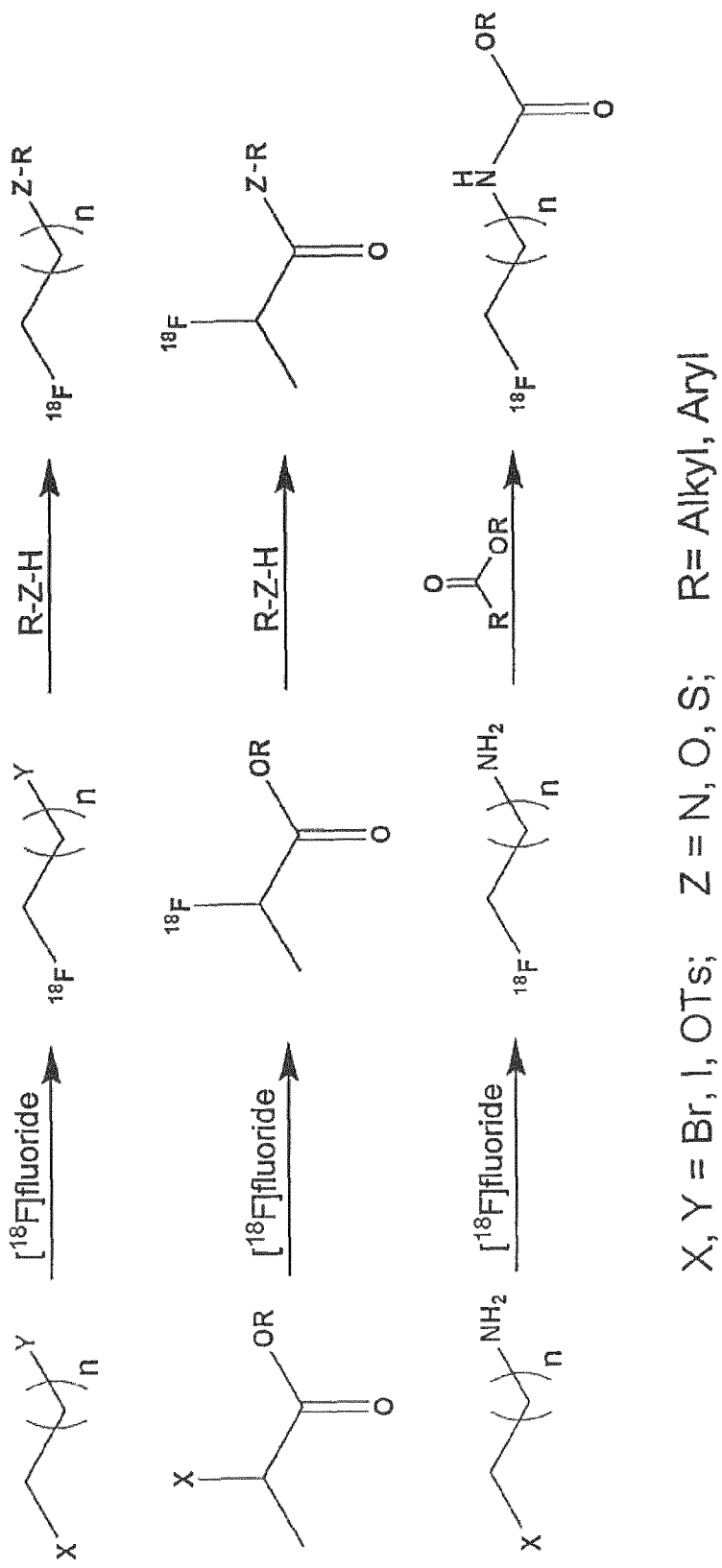
FIG. 2: $^{18}$F-Fluorination via prosthetic groups.
Figure 3:
FIG. 3: $^{18}$F-prosthetic groups for peptides.
Figure 3:
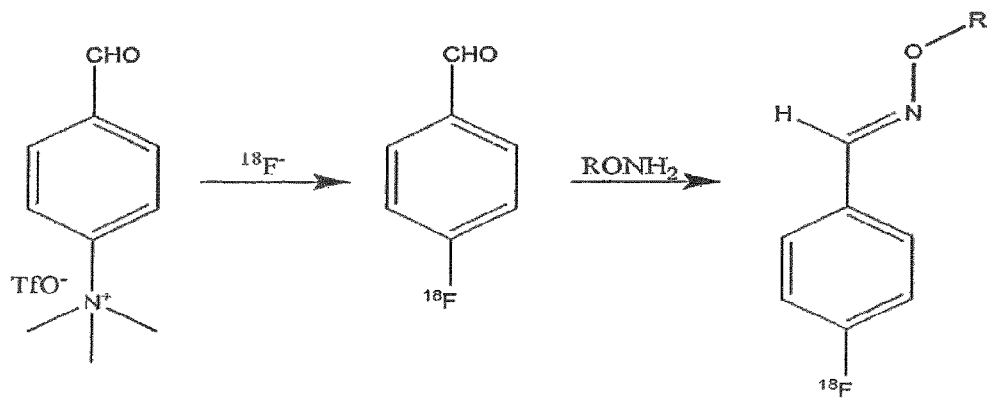
Figure 3:
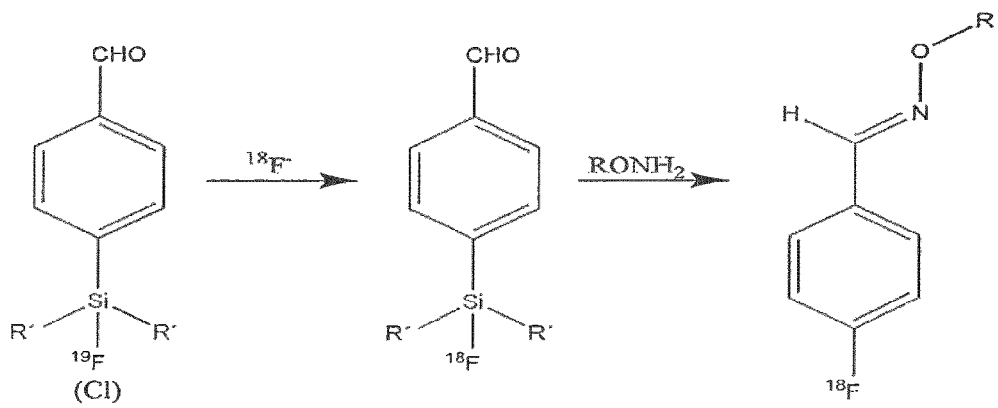
Figure 4:
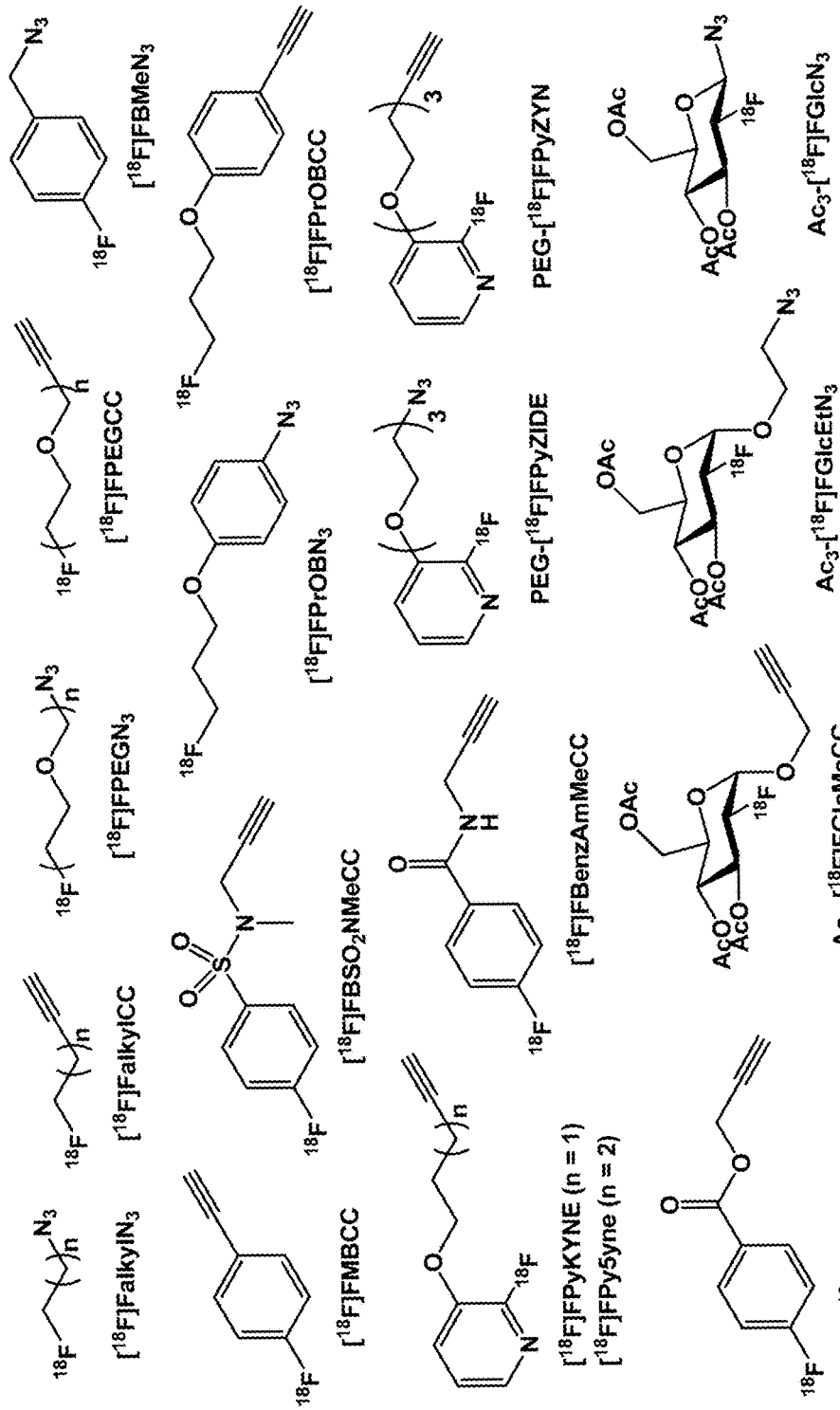
FIG. 4: $^{18}$F-Labelled Prosthetic Groups using "Click Chemistry".
Figure 5:
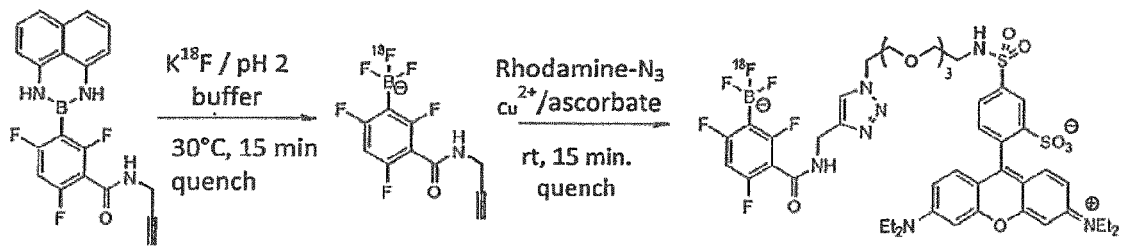
FIG. 5: Formation of [$^{18}$F]aryltrifluoroboronates and fluoride sensors.
Figure 5:
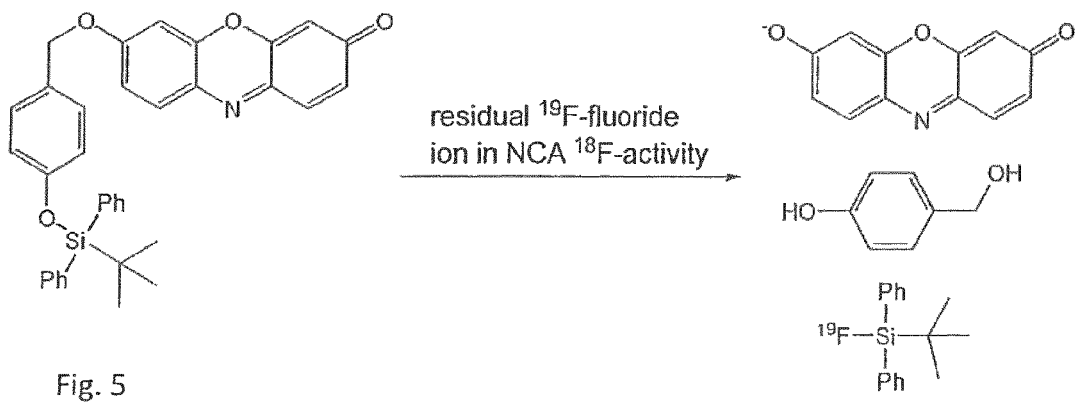
Figure 6:
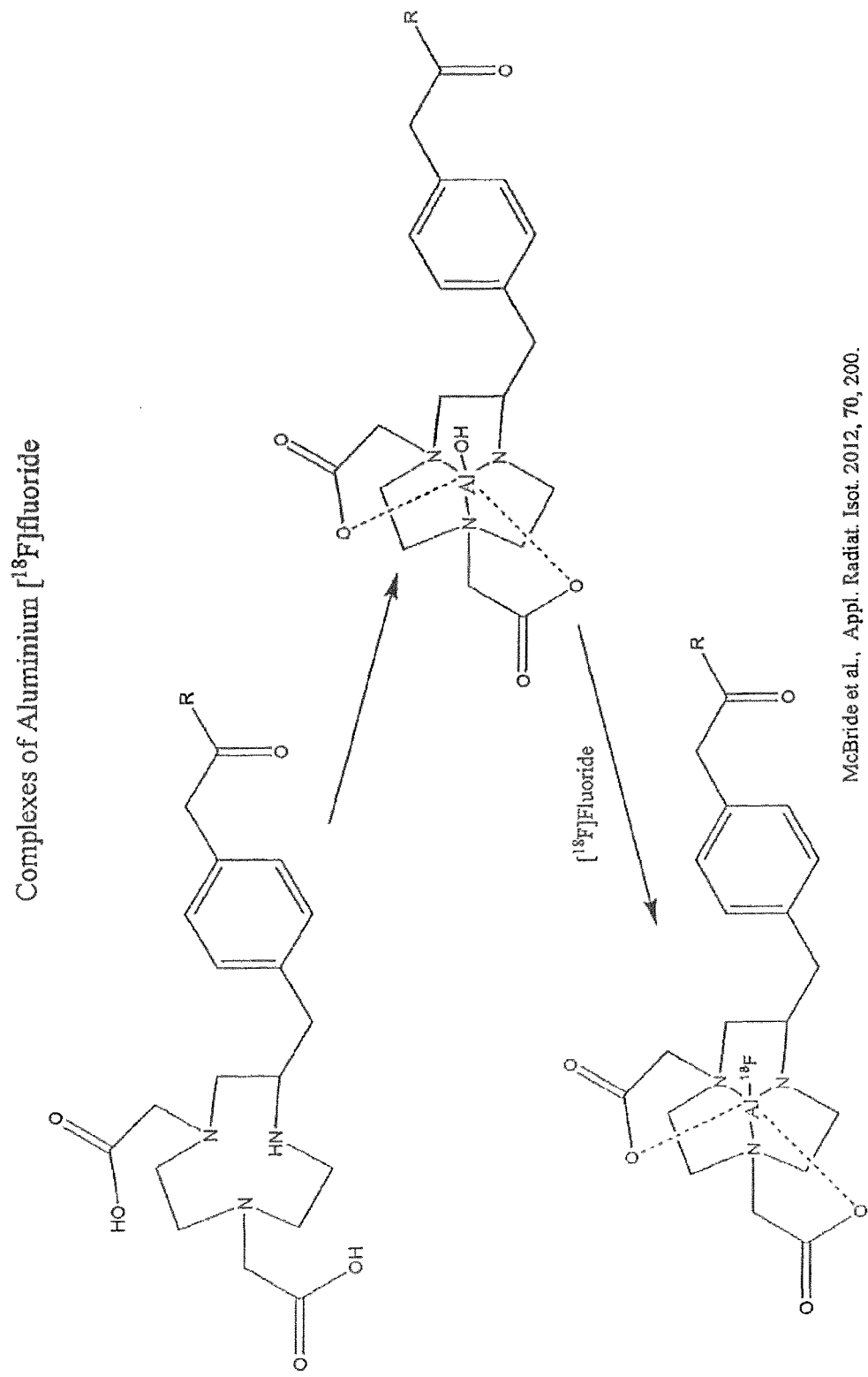
FIG. 6: Complexes of $^{18}$F-Fluorides.
Figure 7:
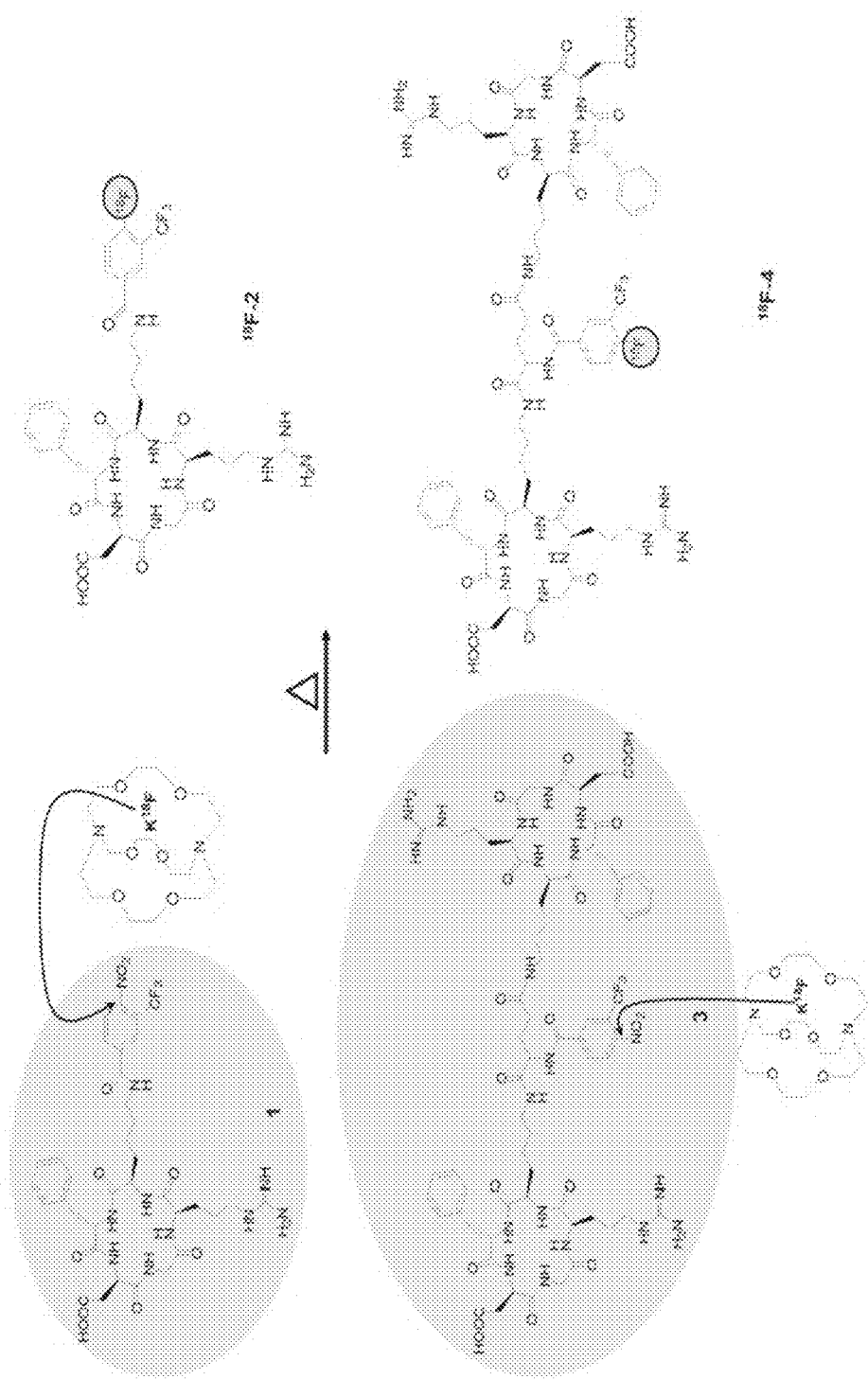
FIG. 7: $^{18}$F-Labelling of RGD peptides.

The present invention relates to radiopharmaceuticals and their use in nuclear medicine as tracers, imaging agents and for the treatment of various disease states of prostate cancer.

Thus, the present invention concerns compounds that are represented by the general Formula (Ia) or (Ib):

Formula (Ia)

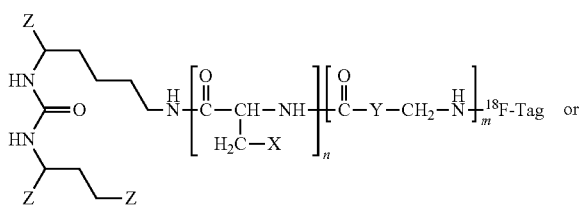

or

Formula (Ib)

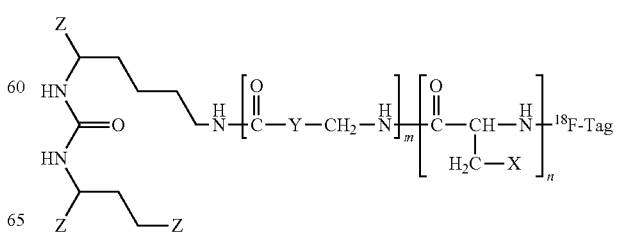

| | |
|---|---|
| n: | 0, 1 |
| m: | 0, 1, 2, 3, 4 with proviso that m + n > 0 |
| Z: | —CO₂H, —SO₂H, —SO₃H, —SO₄H, —PO₂H, —PO₃H, —PO₄H₂ |
| X: | Naphthyl, Phenyl, Biphenyl, Indolyl (=2,3-benzopyrrolyl), Benzothiazolyl |
| Y: | Aryl, Alkylaryl, Cyclopentyl, Cyclohexyl, Cycloheptyl |
¹⁸F-Tag:
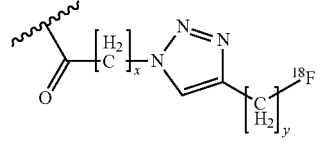
x = 1-5  y = 1-5
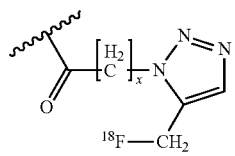
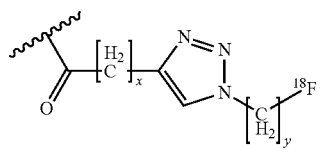
x = 1-5  y = 1-5
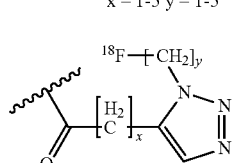
x = 1-5  y = 1-5
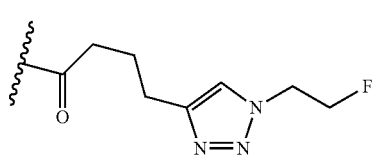 [SMILES: *C(=O)CCCc1cn(CCF)nn1]
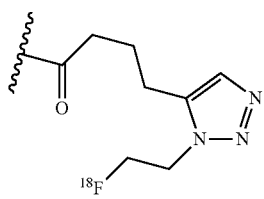 [SMILES: *C(=O)CCCc1cnnn1CC[18F]]
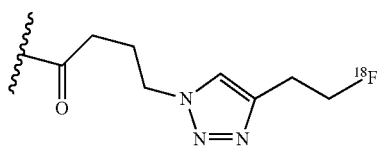 [SMILES: *C(=O)CCCn1cc(CC[18F])nn1]
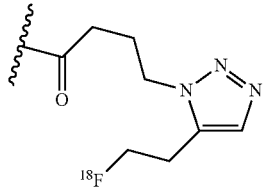 [SMILES: *C(=O)CCCn1nncc1CC[18F]]
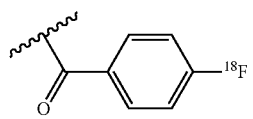
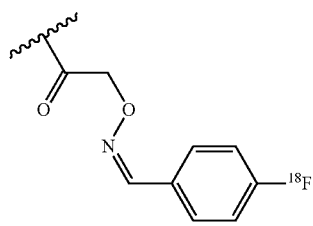 [SMILES: *C(=O)CO/N=C\c1ccc([18F])cc1]
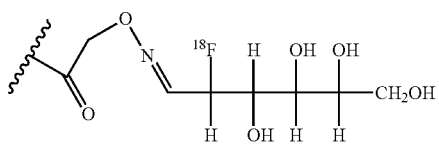
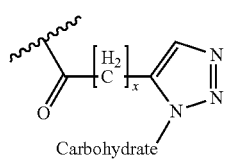
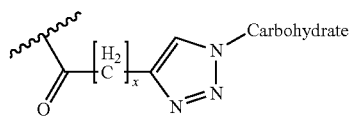
With:
x = 1-5
Carbohydrate:
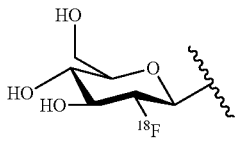
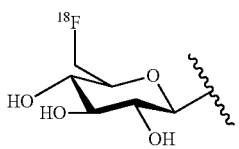
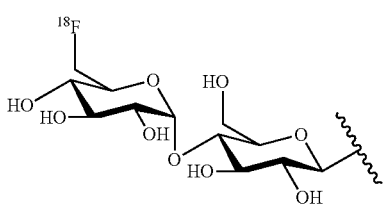

-continued

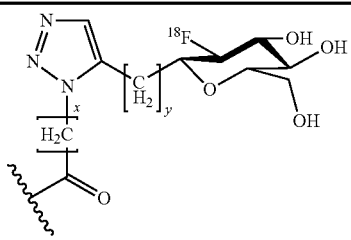

x = 1-5 y = 1-5

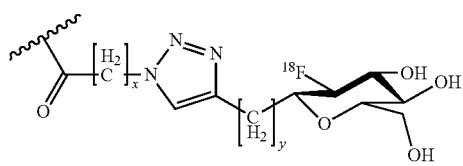

x = 1-5 y = 1-5

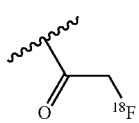 [SMILES: *C(=O)C[18F]]

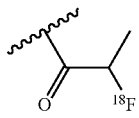 [SMILES: *C(=O)C(C)[18F]]

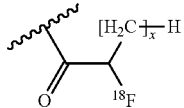

x = 1-10

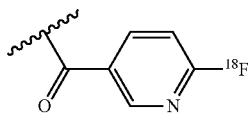

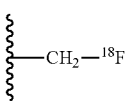

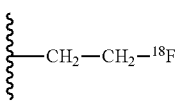

x = 1-10

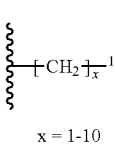

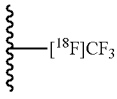

-continued

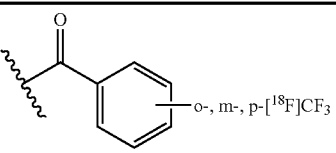

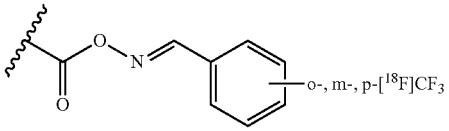

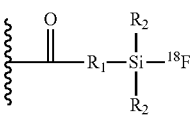

$R_1$: Any alkyl, aryl or arylalkyl linker
especially methyl, 2-ethyl, 3-propyl,
2-, 3-, 4-phenyl, 2-, 3-, 4-phenylmethyl, 2-, 3-, 4-phenylpropyl
$R_2$: Any alkyl or aryl group
especially methyl isopropyl, tert-butyl,
phenyl or 1-naphtyl

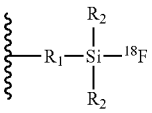

$R_1$: Any alkyl, aryl or arylalkyl linker
especially methyl, 2-ethyl, 3-propyl,
2-, 3-, 4-phenyl, 2-, 3-, 4-phenylmethyl, 2-, 3-, 4-phenylpropyl
$R_2$: Any alkyl or aryl group
especially methyl isopropyl, tert-butyl,
phenyl or 1-naphtyl

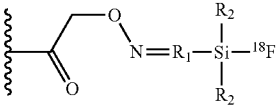

$R_1$: Any alkyl, aryl or arylalkyl linker
especially methyl, 2-ethyl, 3-propyl,
2-, 3-, 4-phenyl, 2-, 3-, 4-phenylmethyl, 2-, 3-, 4-phenylpropyl
$R_2$: Any alkyl or aryl group
especially methyl isopropyl, tert-butyl,
phenyl or 1-naphtyl

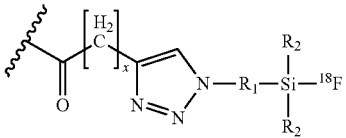

x = 1-5

$R_1$: Any alkyl, aryl or arylalkyl linker
especially methyl, 2-ethyl, 3-propyl,
2-, 3-, 4-phenyl, 2-, 3-, 4-phenylmethyl, 2-, 3-, 4-phenylpropyl
$R_2$: Any alkyl or aryl group
especially methyl isopropyl, tert-butyl,
phenyl or 1-naphtyl

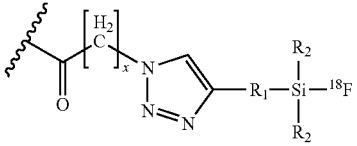

x = 1-5

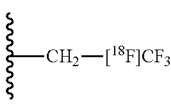

R₁: Any alkyl, aryl or arylalkyl linker
especially methyl, 2-ethyl, 3-propyl,
2-, 3-, 4-phenyl, 2-, 3-, 4-phenylmethyl, 2-, 3-, 4-phenylpropyl
R₂: Any alkyl or aryl group
especially methyl isopropyl, tert-butyl,
phenyl or 1-naphtyl

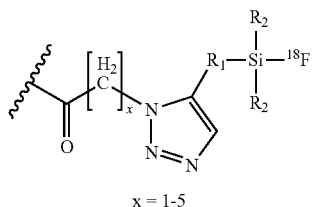

x = 1-5

R₁: Any alkyl, aryl or arylalkyl linker
especially methyl, 2-ethyl, 3-propyl,
2-, 3-, 4-phenyl, 2-, 3-, 4-phenylmethyl, 2-, 3-, 4-phenylpropyl
R₂: Any alkyl or aryl group
especially methyl isopropyl, tert-butyl,
phenyl or 1-naphtyl

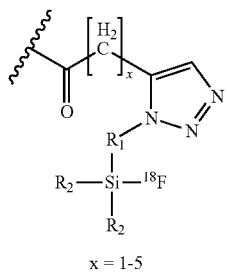

x = 1-5

R₁: Any alkyl, aryl or arylalkyl linker
especially methyl, 2-ethyl, 3-propyl,
2-, 3-, 4-phenyl, 2-, 3-, 4-phenylmethyl, 2-, 3-, 4-phenylpropyl
R₂: Any alkyl or aryl group
especially methyl isopropyl, tert-butyl,
phenyl or 1-naphtyl If not stated otherwise, in the present invention the "alkyl" residue (preferably: $C_1$ to $C_{10}$) can be linear or branched, unsubstituted or substituted. Preferred alkyl residues are methyl, ethyl, n-propyl, iso-propyl, n-butyl, tert-butyl, n-pentanyl, n-hexanyl. The same also applies to the corresponding cycloalkyl compounds having preferably 3 to 10 carbon atoms.

"Aryl" refers to an aromatic monocyclic or polycyclic ring system having 6 to 14 carbon atoms, preferably 6 to 10 carbon atoms. The aryl group can be substituted, where appropriate, with one or several ring substituents, like alkyl groups. Preferred aryl groups are phenyl, benzyl or naphthyl.

Although it is preferred that the Z-Group is —CO2H it may be easily replaced with biosteric replacements such as —SO²H, —SO³H, —SO⁴H, —PO²H, —PO³H, —PO⁴H2, see e.g. "The Practice of Medicinal Chemistry" (Academic Press New York, 1996), page 203.

Within the meaning of the invention, all residues are considered combinable unless stated otherwise in the definition of the residues. All conceivable subgroupings thereof are considered to be disclosed.

The ¹⁸F-Tags of the above Table comprising triazoles exist in two isomeric forms which belong both to the invention and are illustrated by the given formulas.

In a preferred embodiment, the motif specifically binding to cell membranes of neoplastic cells is a motif specifically binding to cell membranes of cancerous cells, preferable wherein said motif comprises a prostate-specific membrane antigen (PSMA), in particular wherein said PSMA comprises a glutamate-urea-lysine motif according to the following formula in Scheme 1.

Thus, preferred molecules of the present invention consist of three principle components (Scheme 1): the hydrophilic PSMA binding motif (Glu-Urea-Lys=Glu-NH—CO—NH-Lys), a variable linker and the ¹⁸F-Tag.

Scheme 1: Structure of Preferred Compounds of the Present Invention

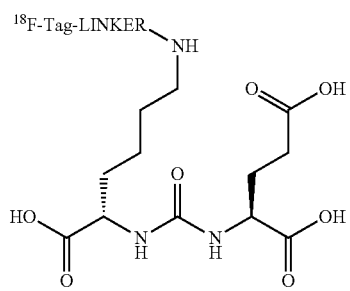

The different preferred linkers are shown below, wherein R=Glu-Urea-Lys and R'=¹⁸F-Tag, as shown above.

MB2 Linker

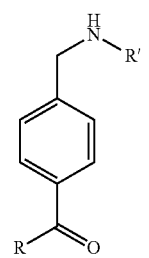

MB3 Linker

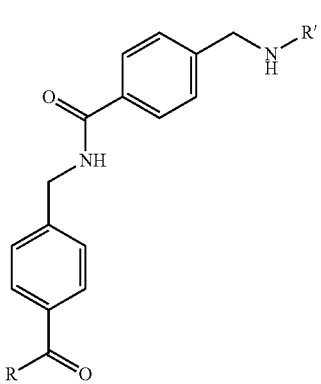

MB4 Linker
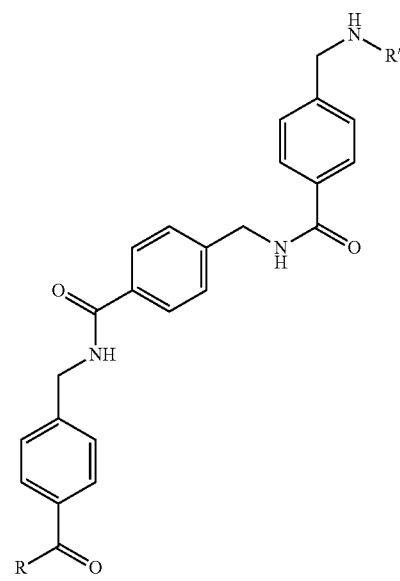
MB10 Linker
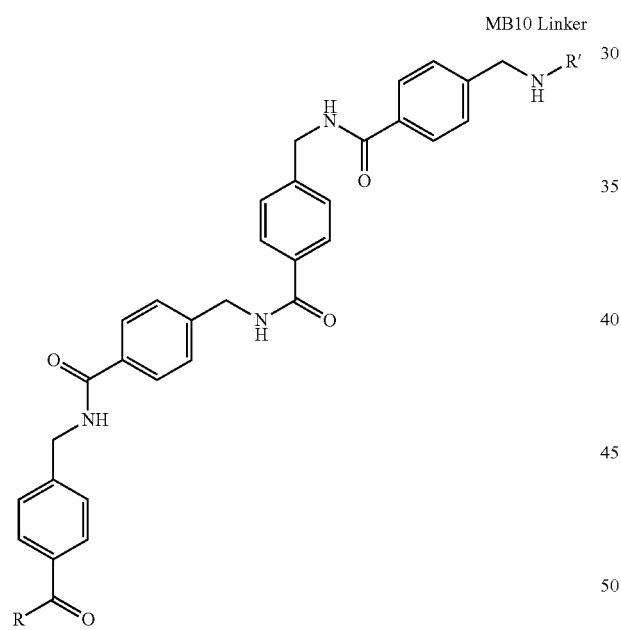
MB17 Linker
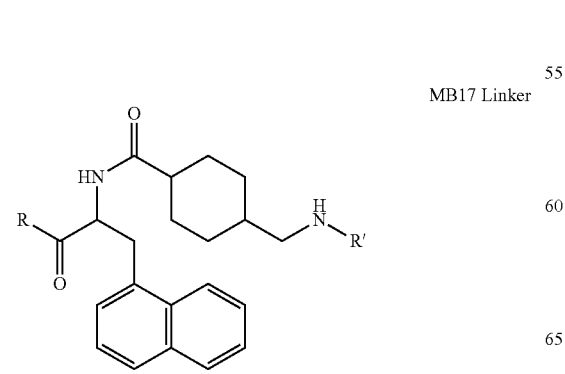
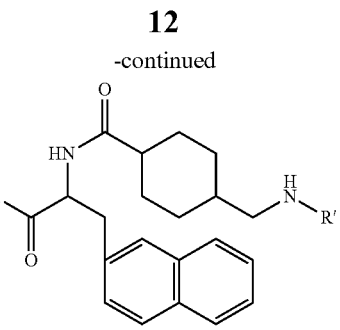
MB22 Linker
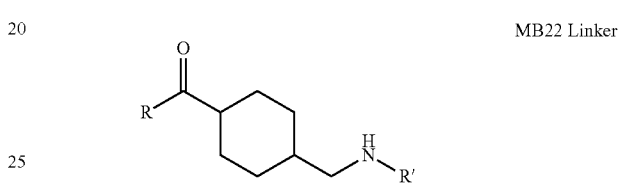
MB16 Linker
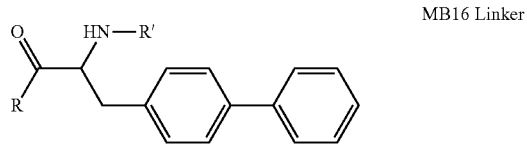
MB24
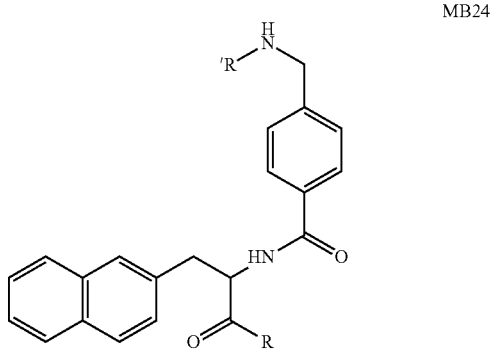

-continued
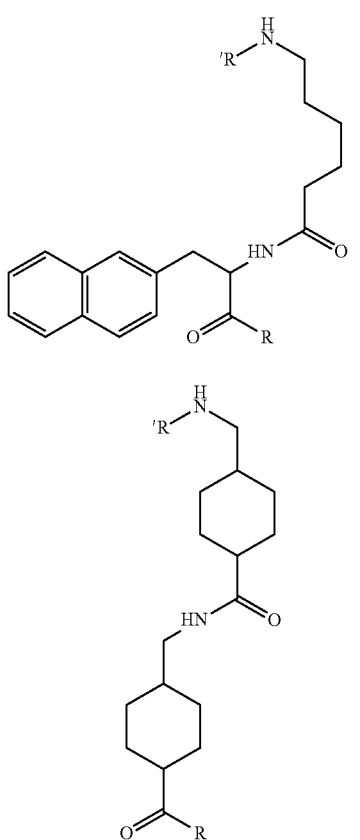
MB25
MB31
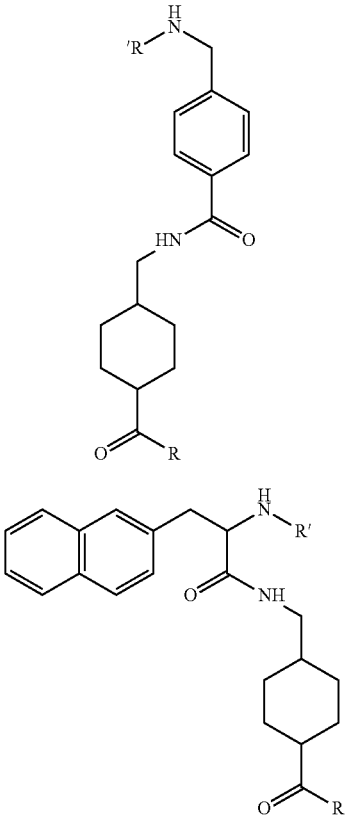
MB33
MB35
Preferred compounds of the present invention are shown below (with X, Y and Z as defined above in the Table in connection with Formula I(a) and I(b))
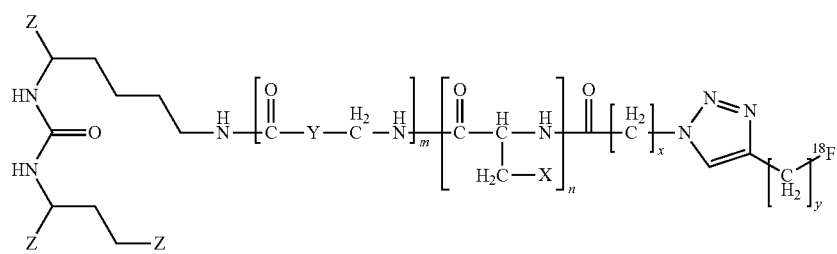
x = 1-5
y = 1-5
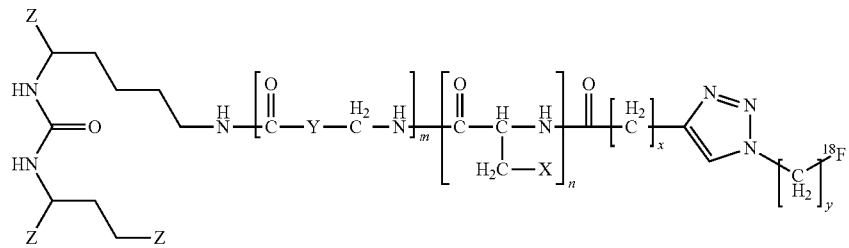
x = 1-5
y = 1-5

-continued
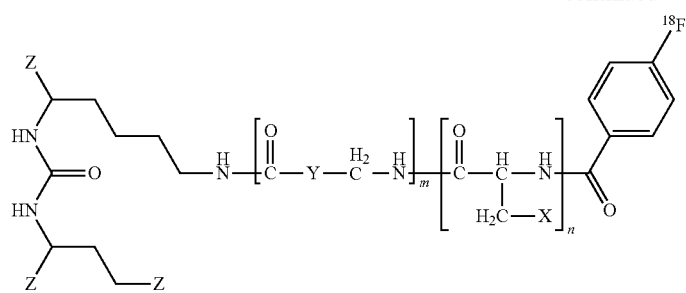
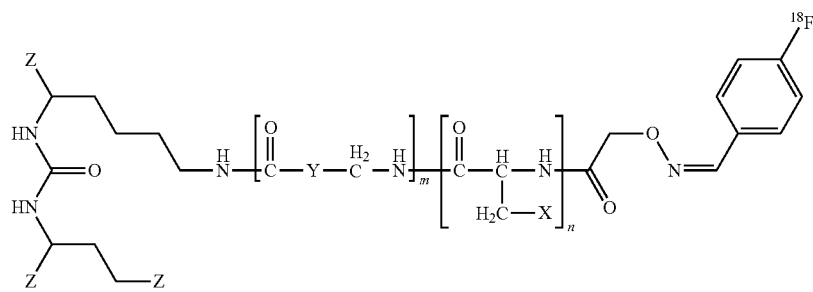
bzw. FDG
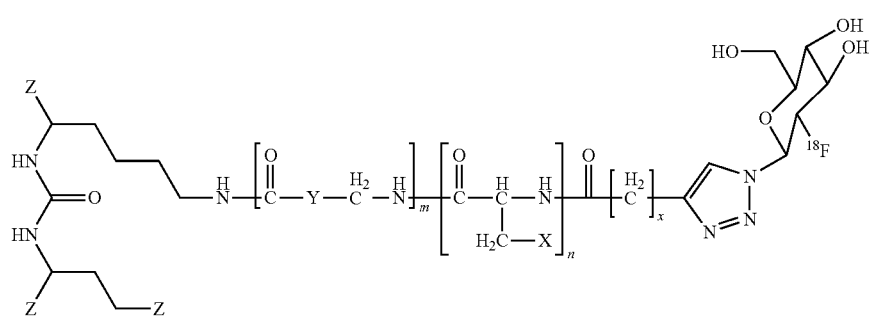
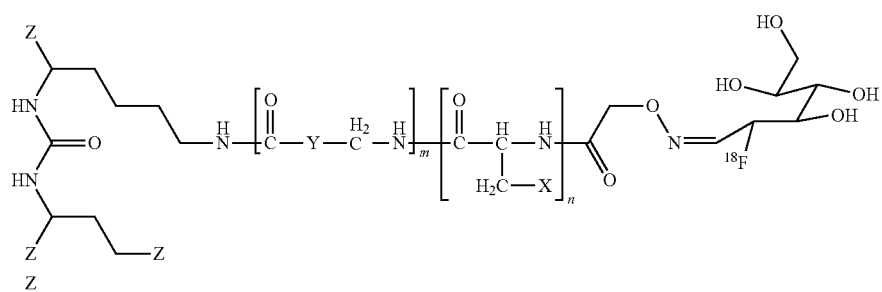
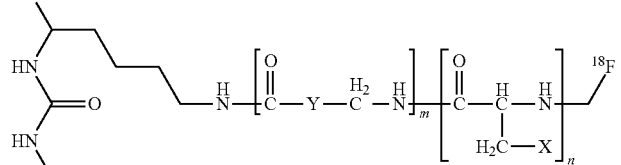
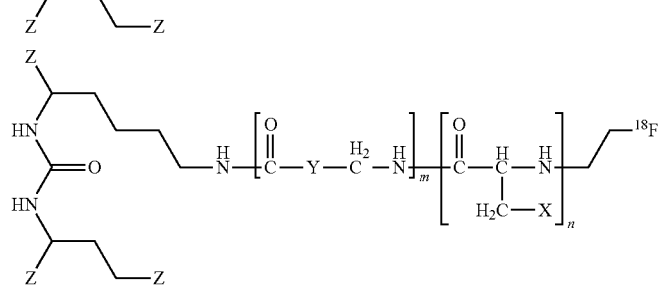

-continued
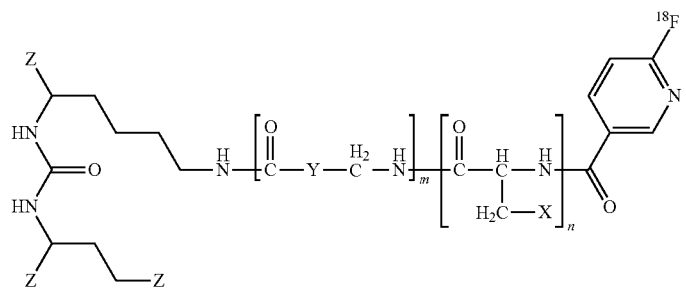
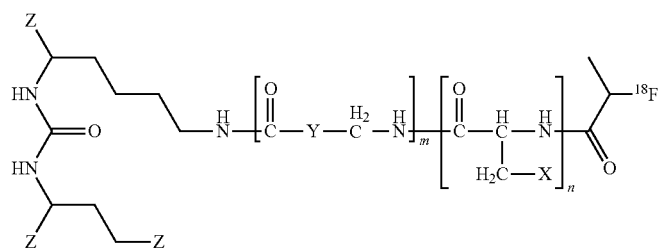
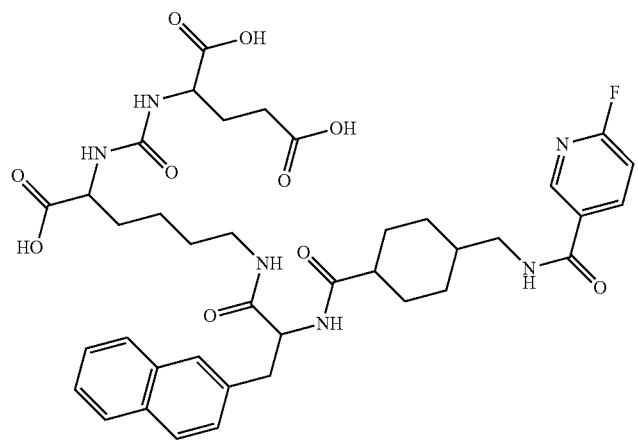
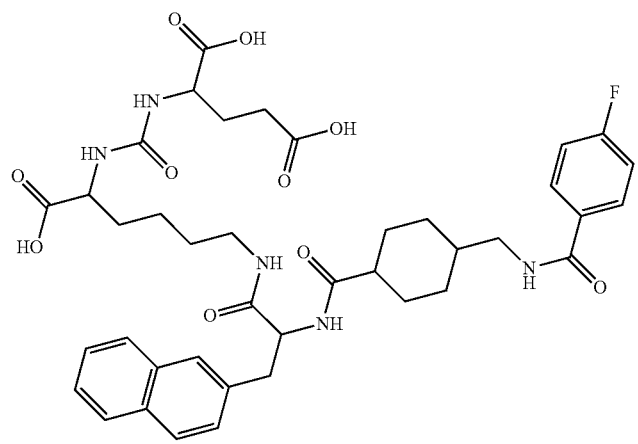

19
20
-continued
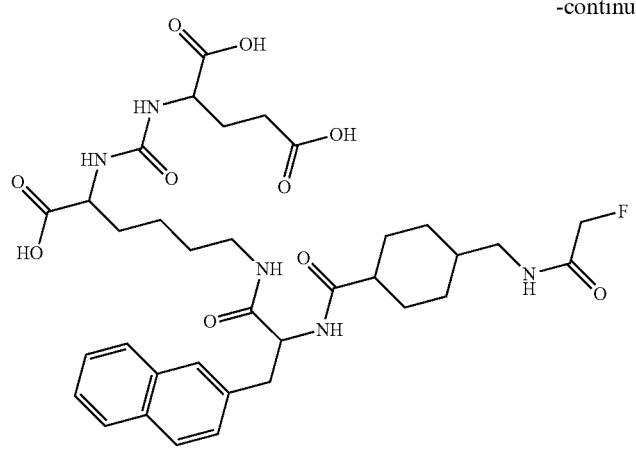
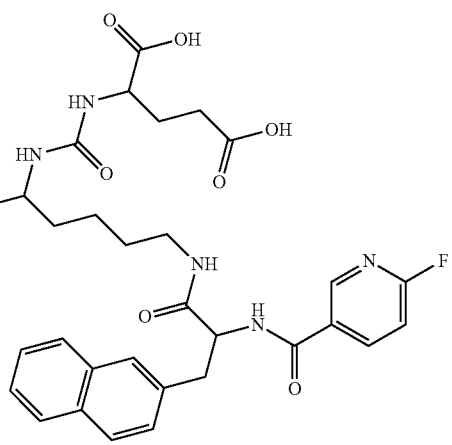
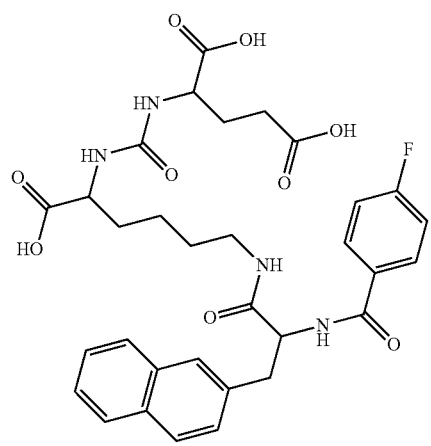
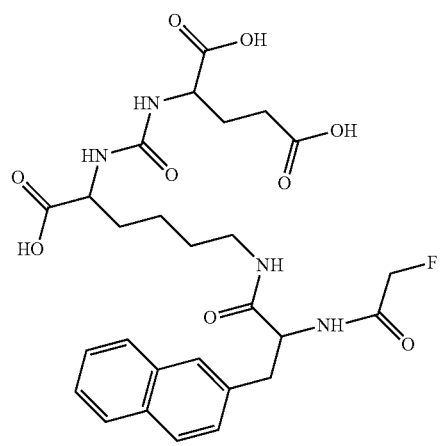
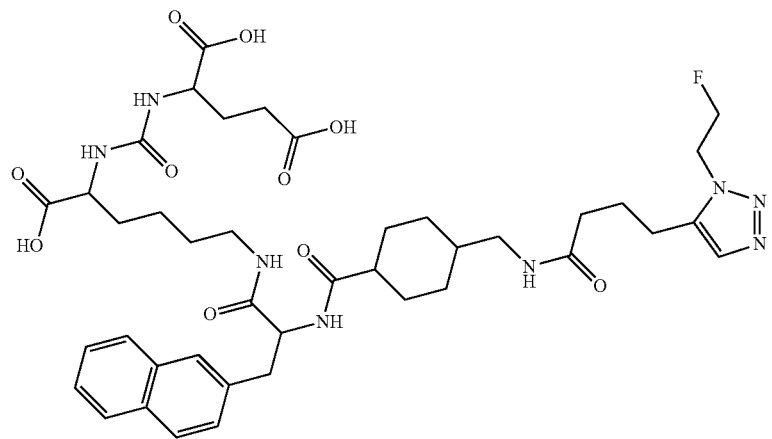

-continued
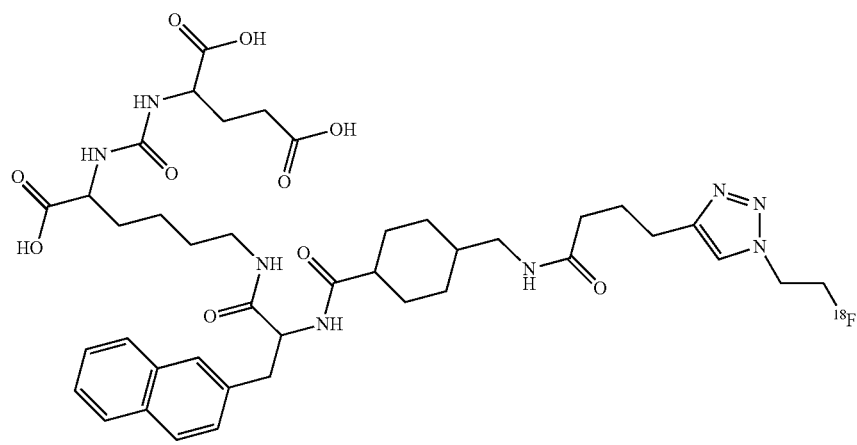
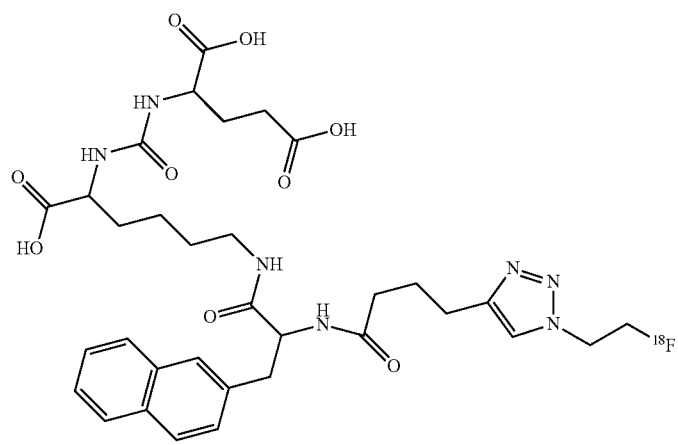
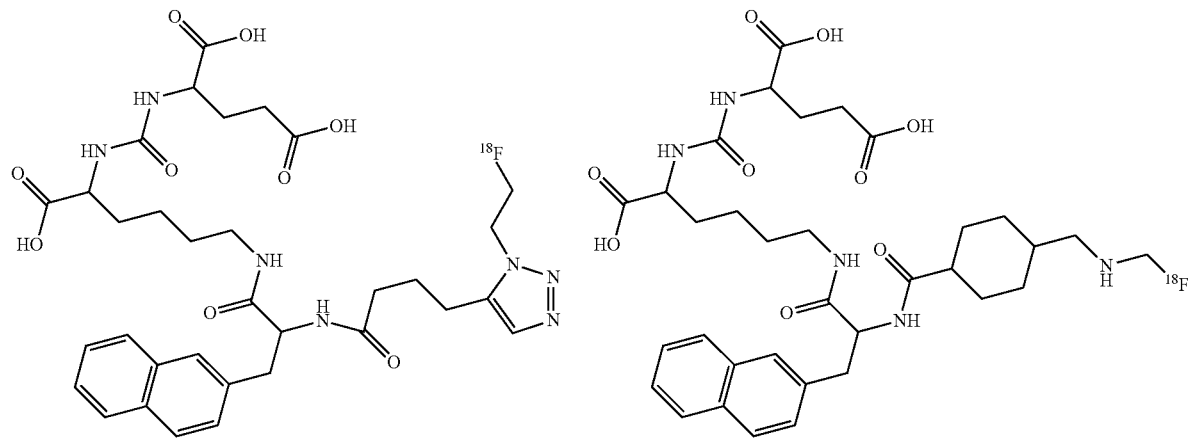

-continued
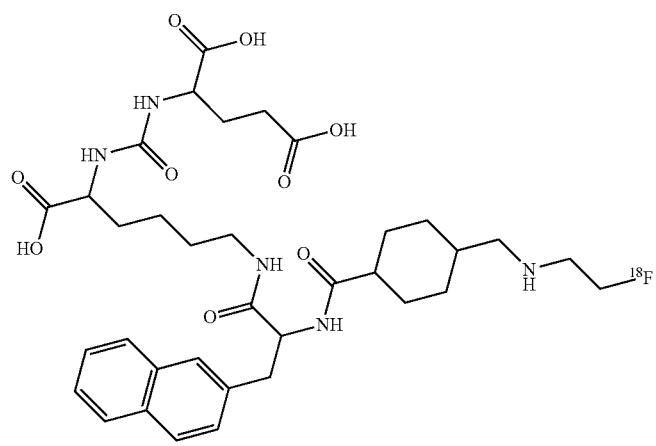
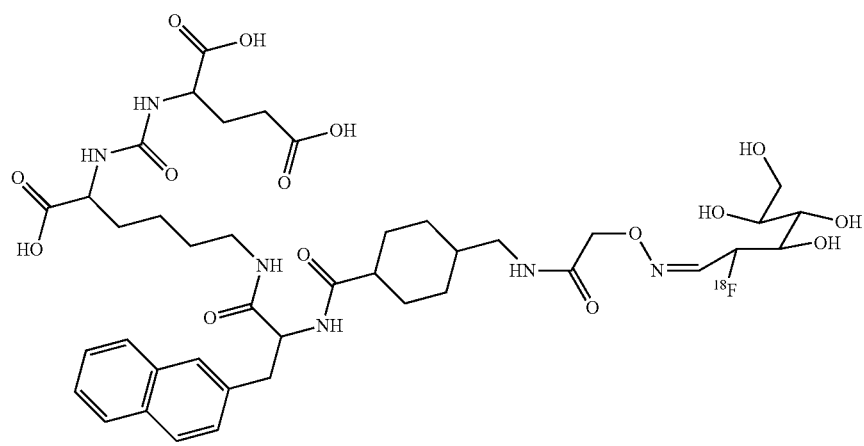
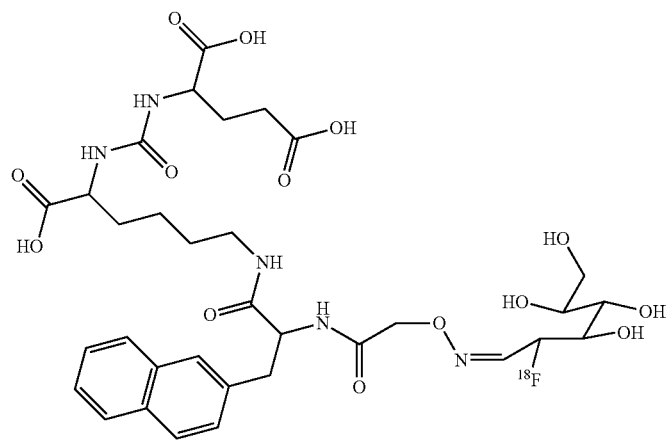
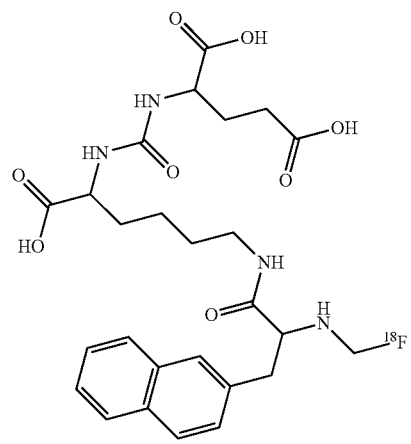

-continued

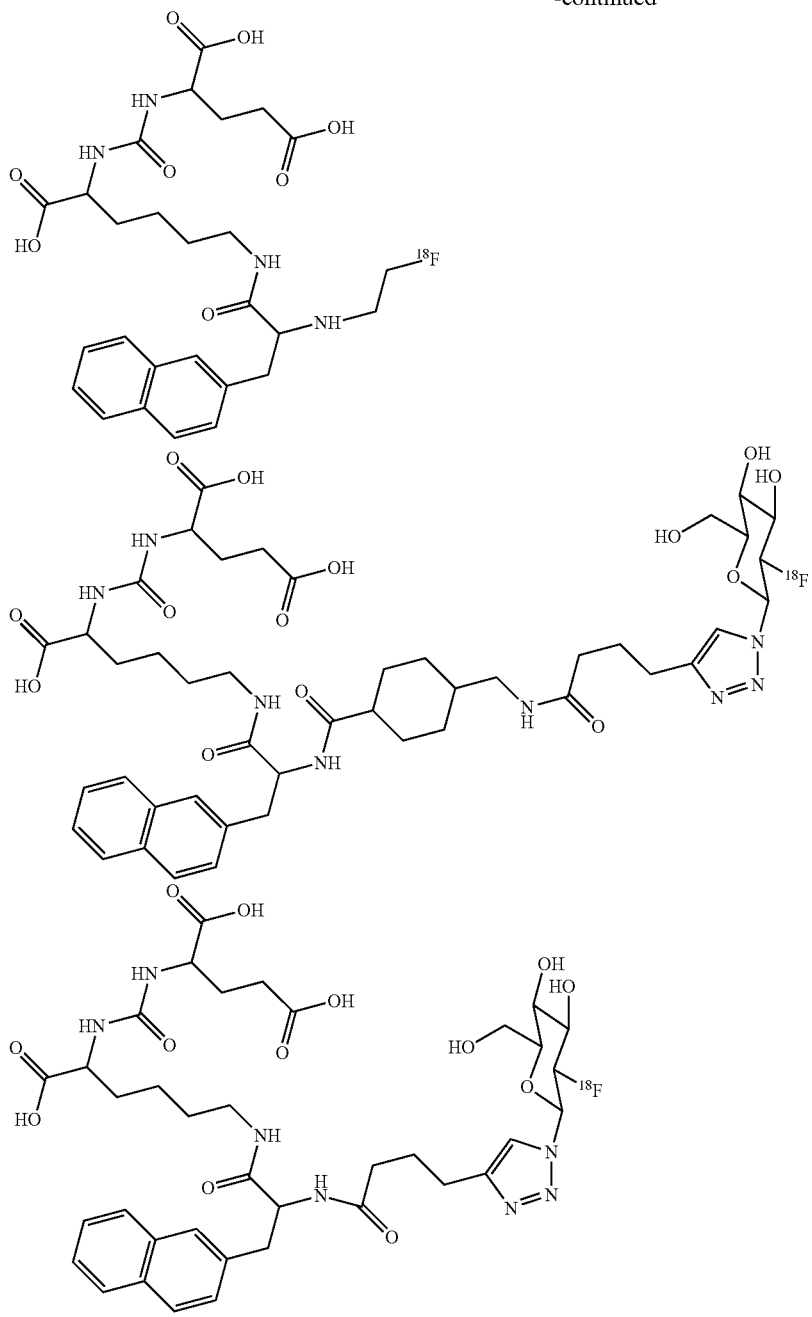

The invention also relates to pharmaceutically acceptable salts of the compounds of general formula (Ia) and/or (Ib). The invention also relates to solvates of the compounds, including the salts as well as the active metabolites thereof and, where appropriate, the tautomers thereof according to general formula (Ia) and/or (Ib) including prodrug formulations.

A "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, carbonate, chloride, gluconate, glutamate, lactate, laurate, malate or tartrate.

The term "prodrug" refers to a precursor of a drug that is a compound which upon administration to a patient, must undergo chemical conversion by metabolic processes before becoming an active pharmacological agent. Illustrative prodrugs of compounds in accordance with Formula (Ia) and/or (Ib) are esters and amides, preferably alkyl esters of fatty acid esters. Prodrug formulations here comprise all substances which are formed by simple transformation including hydrolysis, oxidation or reduction either enzymatically, metabolically or in any other way. A suitable prodrug contains e.g. a substance of general formula (Ia) and/or (Ib) bound via an enzymatically cleavable linker (e.g. carbamate, phosphate, N-glycoside or a disulfide group) to a dissolution-improving substance (e.g. tetraethylene glycol, saccharides, formic acids or glucuronic acid, etc.). Such a prodrug of a compound according to the invention can be applied to a patient, and this prodrug can be transformed into a substance of general formula (la) and/or (lb) so as to obtain the desired pharmacological effect.

Some compounds of Formula (la) and/or (lb) are encompassed in form of the racemates, their enantiomers and optionally in form of their diastereomers and all possible mixtures thereof.

According to the invention all chiral C-atoms shall have D- and/or L-configuration; also combinations within one compound shall be possible, i.e. some of the chiral C-atoms may be D- and others may be L-configuration.

The obtained compounds can be optionally separated by known methods (e.g. Allinger, N. L. and Ellie/E. L. in "Topics in Stereochemistry" Vol. 6, Wiley Interscience, 1971) in their enantiomers and/or diasteromers. One possible method of enantiomeric separation is the use of chromatography.

The invention also relates to pharmaceutical preparations which contain a therapeutically effective amount of the active ingredients (compound according to the invention of formula (la) or (lb) together with organic or inorganic solid or liquid, pharmaceutically acceptable carriers which are suited for the intended administration and which interact with the active ingredients without drawbacks.

The phrase "pharmaceutically acceptable" is employed herein to refer to those compounds, material, compositions, and/or dosage forms which are, within the scope of sound medical judgment, suitable for use in contact with the tissues of a patient without excessive toxicity, irritation, allergic response, or other problem or complication, commensurate with a reasonable benefit/risk ratio.

A "patient" includes an animal, such as a human, monkey, cow, horse, cat or dog. The animal can be a mammal such as a non-primate and a primate (e.g., monkey and human). In one embodiment, a patient is a human being.

In general, the Formula (la) or (lb) compound or pharmaceutical compositions thereof, may be administered orally or via a parenteral route, usually injection or infusion.

A "parenteral administration route" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticuluare, subcapsular, subarachnoid, intraspinal and intrasternal injection and infusion.

The dosage of the compounds according to the invention is determined by the physician on the basis of the patient-specific parameters, such as age, weight, sex, severity of the disease, etc. The dosage is preferably from 0.00001 mg/kg to 100 mg/kg body weight, preferably from 0.001 to 50 mg/kg body weight and most preferably from 0.01 to 1.0 mg/kg body weight.

Corresponding to the kind of administration, the medicament is suitably formulated, e.g. in the form of solutions or suspensions, simple tablets or dragees, hard or soft gelatine capsules, suppositories, ovules, preparations for injection, which are prepared according to common galenic methods.

The compounds according to the invention can be formulated, where appropriate, together with further active substances and with excipients and carriers common in pharmaceutical compositions, e.g.—depending on the preparation to be produced—talcum, gum arabic, lactose, starch, magnesium stearate, cocoa butter, aqueous and non-aqueous carriers, fatty bodies of animal or vegetable origin, paraffin derivatives, glycols (in particular polyethylene glycol), various plasticizers, dispersants or emulsifiers, pharmaceutically compatible gases (e.g. air, oxygen, carbon dioxide, etc.), preservatives.

In order to produce liquid preparations, additives, such as sodium chloride solution, ethanol, sorbitol, glycerine, olive oil, almond oil, propylene glycol or ethylene glycol, can be used.

When solutions for infusion or injection are used, they are preferably aqueous solutions or suspensions, it being possible to produce them prior to use, e.g. from lyophilized preparations which contain the active substance as such or together with a carrier, such as mannitol, lactose, glucose, albumin and the like. The ready made solutions are sterilized and, where appropriate, mixed with excipients, e.g. with preservatives, stabilizers, emulsifiers, solubilizers, buffers and/or salts for regulating the osmotic pressure. The sterilization can be obtained by sterile filtration using filters having a small pore size according to which the composition can be lyophilized, where appropriate. Small amounts of antibiotics can also be added to ensure the maintenance of sterility.

The phrases "effective amount" or "therapeutically-effective amount" as used herein means that amount of a compound, material, or composition comprising a compound of the invention, or other active ingredient which is effective for producing some desired therapeutic effect in at least a sub-population of cells in an animal at a reasonable benefit/risk ratio applicable to any medical treatment. A therapeutically effective amount with respect to a compound of the invention means that amount of therapeutic agent alone, or in combination with other therapies, that provides a therapeutic benefit in the treatment of prevention of a disease. Used in connection with a compound of the invention, the term can encompass an amount that improves overall therapy, reduces or avoids symptoms or causes of disease, or enhances the therapeutic efficacy of or synergies with another therapeutic agent.

As used herein, the terms "treating" or "treatment" is intended to encompass also diagnosis, prophylaxis, prevention, therapy and cure.

The terms "prevent," "preventing," and "prevention" refer to the prevention of the onset, recurrence, or spread of the disease in a patient resulting from the administration of a prophylactic or therapeutic agent.

As noted above, compounds according Formula (la) or (lb) are suitable for use as radio-imaging agents or as therapeutics for the treatment of rapidly proliferating cells, for example, PSMA expressing prostate cancer cells. According to the present invention they are called "radiopharmaceuticals".

Preferred imaging methods are positron emission tomography (PET) or single photon emission computed tomography (SPECT).

Accordingly, in one embodiment, a pharmaceutical composition is provided including a compound of Formula (la) or Formula (lb), a salt, solvate, stereoisomer, or tautomer thereof, and a pharmaceutically acceptable carrier. Accordingly, a pharmaceutical composition is provided, which is suitable for in vivo imaging and radiotherapy. Suitable pharmaceutical compositions may contain the compound of Formula (la) and/or (lb) in an amount sufficient for imaging, together with a pharmaceutically acceptable radiological vehicle. The radiological vehicle should be suitable for injection or aspiration, such as human serum albumin; aqueous buffer solutions, e.g., tris(hydromethyl) aminomethane (and its salts), phosphate, citrate, bicarbonate, etc;

sterile water physiological saline; and balanced ionic solutions containing chloride and or bicarbonate salts or normal blood plasma cautions such as calcium potassium, sodium and magnesium.

The concentration of the imaging agent or the therapeutic agent in the radiological vehicle should be sufficient to provide satisfactory imaging. For example, when using an aqueous solution, the dosage is about 1.0 to 100 millicuries. The actual dose administered to a patient for imaging or therapeutic purposes, however, is determined by the physician administering treatment. The imaging agent or therapeutic agent should be administered so as to remain in the patient for about 1 hour to 10 days, although both longer and shorter time periods are acceptable. Therefore, convenient ampoules containing 1 to 10 mL of aqueous solution may be prepared.

Imaging may be carried out in the normal manner, for example by injecting a sufficient amount of the imaging composition to provide adequate imaging and then scanning with a suitable imaging or scanning machine, such as a tomograph or gamma camera. In certain embodiments, a method of imaging a region in a patient includes the steps of: (i) administering to a patient a diagnostically effective amount of a compound complexed with a radionuclide; exposing a region of the patient to the scanning device; and (ii) obtaining an image of the region of the patient. In certain embodiments of the region imaged is the head or thorax. In other embodiments, the compounds and complexes of Formula l(a) and/or (lb) target the PSMA protein.

Thus, in some embodiments, a method of imaging tissue such as spleen tissue, kidney tissue, or PSMA-expressing tumor tissue is provided including contacting the tissue with a complex synthesized by contacting a radionuclide and a Formula (la) and/or Formula (lb) compound.

The amount of the compound of the present invention, or its salt, solvate, stereoisomer, or tautomer that is administered to a patient depends on several physiological factors that are routinely used by the physician, including the nature of imaging to be carried out, tissue to be targeted for imaging or therapy and the body weight and medical history of the patient to be imaged or treated using a radiopharmaceutical.

Accordingly in another aspect, the invention provides a method for treating a patient by administering to a patient a therapeutically effective amount of a Formula (la) and/or (lb) compound complexed to a radionuclide, or a pharmaceutically acceptable salt or solvate of the complex to treat a patient suffering from a cell proliferative disease or disorder. Specifically, the cell proliferative disease or disorder to be treated or imaged using a compound, pharmaceutical composition or radiopharmaceutical in accordance with this invention is a cancer, for example, prostate cancer and/or prostate cancer metastasis in e.g. lung, liver, kidney, bones, brain, spinal cord, bladder, etc.

The synthesis of the compounds of the present invention is carried out according to methods well known in the prior art (e.g. Hugenberg et al., J. of Medicinal Chemistry, 2013, 56, pp. 6858-6870). General methods for $^{18}$F-labelling of various macromolecules are shown in FIG. 1-7. In addition, reference is made to Schubiger et al., PET Chemistry: The Driving Force in Molecular Imaging, Ernst Schering Research Foundation, Workshop 62, Springer Verlag, ISSN 0947-6075; Ross et al., Current Radiopharmaceuticals, 2010, 3, 202-223; Kühnast et al., Current Radiopharm 3, 2010, 174; Bernard-Gauthier et al., BioMed Research International, 2014, 1; Maschauer and Prante, BioMed Research International, 2014, 1; Olberg et al., J. Med. Chem., 2010, 53, 1732; Rostovtsev et al., Angew. Chem., 2002, 114, 2708; Smith and Greaney, Org. Lett., 2013, 15, 4826. Thus, a person skilled in the art would be able to choose the right $^{18}$F-labelling depending on the starting molecule. The synthesis of the specific linker molecules is shown in EP 13004991 to which reference is made.

The synthesized compounds are chemically characterized by RP-HPLC, MS, and/or NMR.

The novel $^{18}$F-tagged imaging agents with structural modifications in the linker region have improved tumor targeting properties and pharmacokinetics. The pharmacophore presents three carboxylic groups able to interact with the respective side chains of PSMA and an oxygen as part of zinc complexation in the active center. Besides these obligatory interactions, the inventors were able to optimize the lipophilic interactions in the linker region.

The preclinical evaluation includes in vitro assays (affinity, internalization) and in vivo experiments (µPET screening and organ distribution).

The compounds of the present invention are better than known reference compounds with regard to kidney clearance and enrichment in the tumor. The binding affinity of PSMA inhibitors of the present invention can be influenced by linker modifications. Two cyclic motives and at least one aromatic moiety in the linker region of the substance seem to be preferable and resulted in the high affinity compounds MB4 and MB17. In this regard, a very promising compound is MB17.

Thus, the compounds of the present invention represent novel PSMA-targeting probes with optimal characteristics which was also confirmed by organ distribution and small animal PET imaging. The compounds of the present invention show a high PSMA-specific tumor uptake. In addition, they are characterized by an early enrichment in the bladder and also the maximum kidney uptake. With regard to therapeutic use, this gives clear clinical advantages for the compounds of the present invention compared to other PSMA-inhibitors. In the PET diagrams the compounds of the present invention, in particular MB17, show a rapid background clearance as well as a substantial reduction of the enrichment in the kidney after 2 hours while it is further accumulated and retained in the PSMA-expressing tumor.

Compounds with promising results are $^{18}$F-PSMA1001/ 1002/1003/1005.

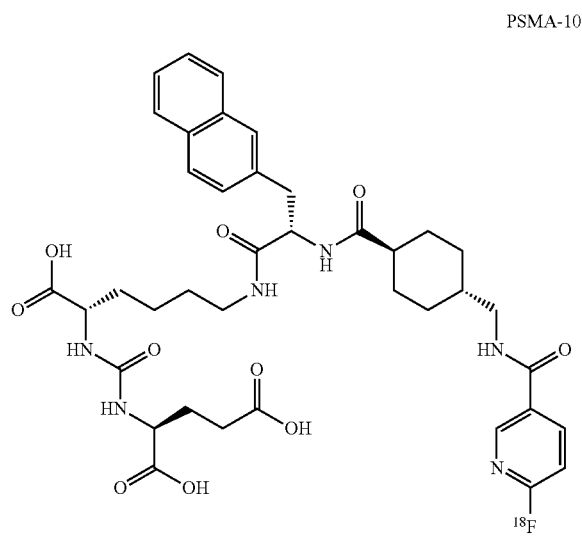

PSMA-1001

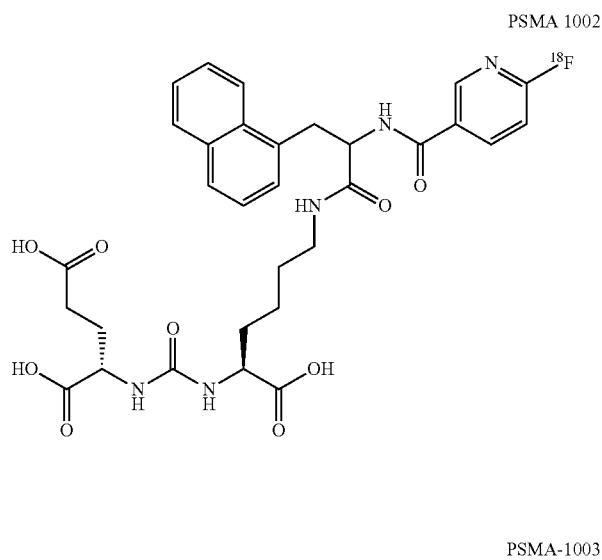

PSMA 1002

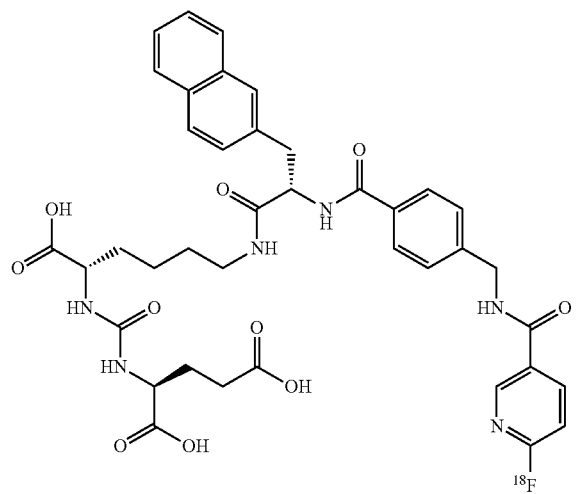

PSMA-1003

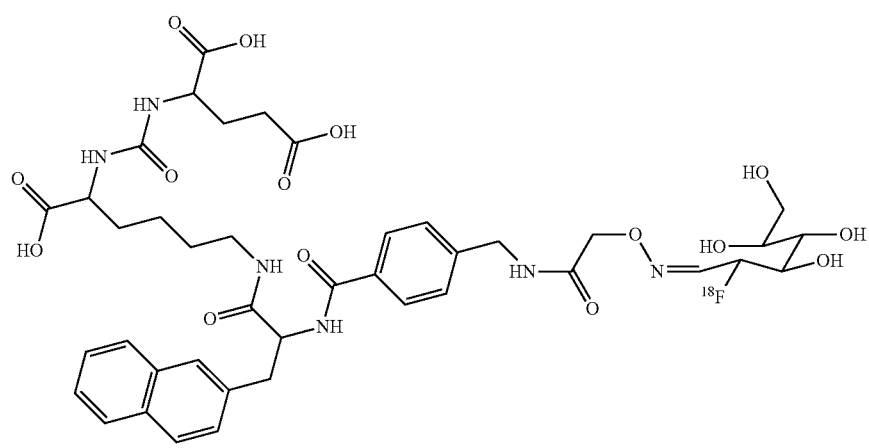

PSMA-1005

Figure 8:
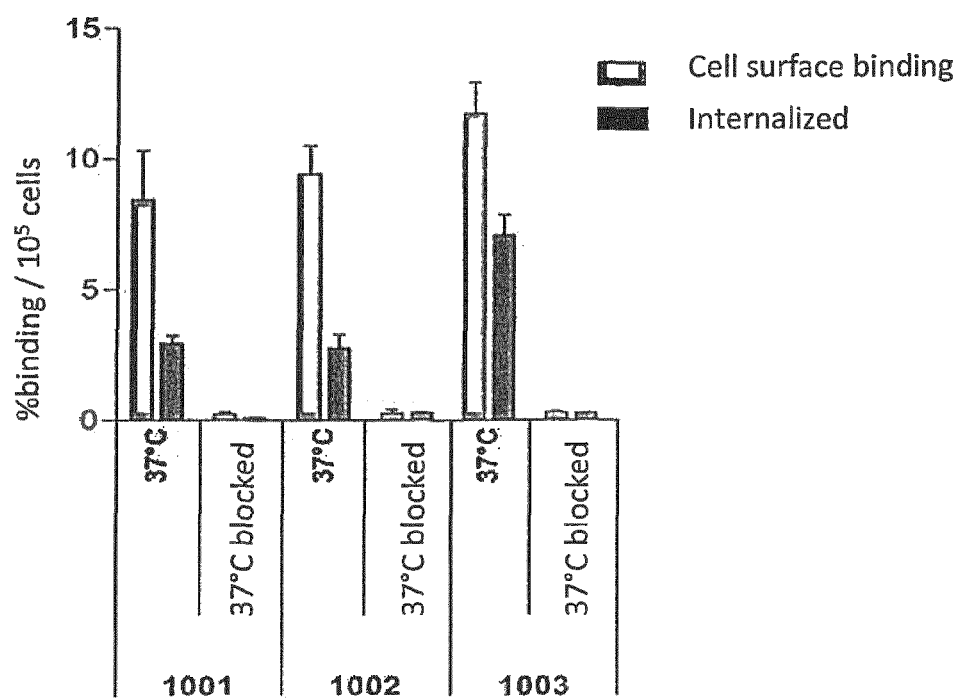
FIG. 8: Internalization of compounds PSMA1001/1002/1003. All compounds were labeled with $^{18}$F, and their specific cell surface binding and internalization properties on LNCaP cells were investigated. Specific cell uptake was determined by blocking with 500 μM-PMPA. Values are expressed as % of applied radioactivity bound to $10^5$ cells. Data are expressed as mean±SD (n=3).

All compounds were labelled with fluorine-18 via 2-[$^{18}$F] fluoronicotinic acid TFP ester in good radiochemical yields. Table A shows that the binding affinity of the PSMA inhibitors prepared so far are essentially the same and in the typical range. Further, all compounds were specifically internalized at 37° C. with rather high cell uptake and internalization values (Table B and FIG. 8). Former studies demonstrated that this is due to the aromatic moieties in the linker region and that besides binding affinity the internalization properties of PSMA-targeting probes are essential for the in vivo tumor uptake and retention. Thus, the compounds investigated exhibit optimal in vitro characteristics for a high contrast PET imaging. Two of the compounds, namely PSMA-1001 and PSMA-1003, were further evaluated by micro-PET. The results are summarized in FIGS. 9 and 10, respectively.

Figure 9:
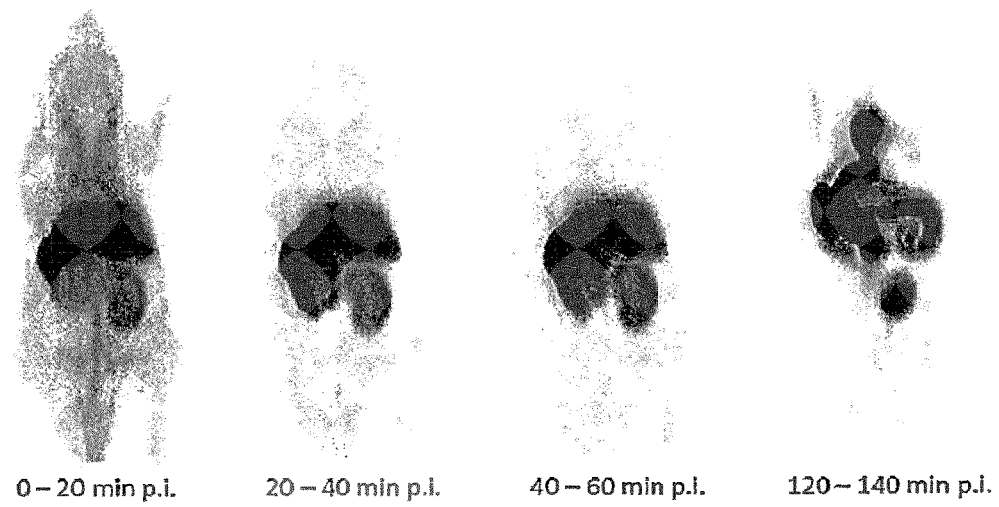
FIG. 9: PET imaging of PSMA-1001. Whole-body coronal microPET images of an athymic male nude mice bearing LNCaP tumor xenografts. The tumor-targeting efficacy and pharmacokinetic properties of $^{18}$F-PSMA-1001 were evaluated by dynamic microPET scans. Approximately 15 MBq/mouse were injected. The respective time-activity-curves of $^{18}$F-PSMA-1001 are shown in the lower part. The values are expressed as mean SUV (standardized uptake values).
Figure 9:
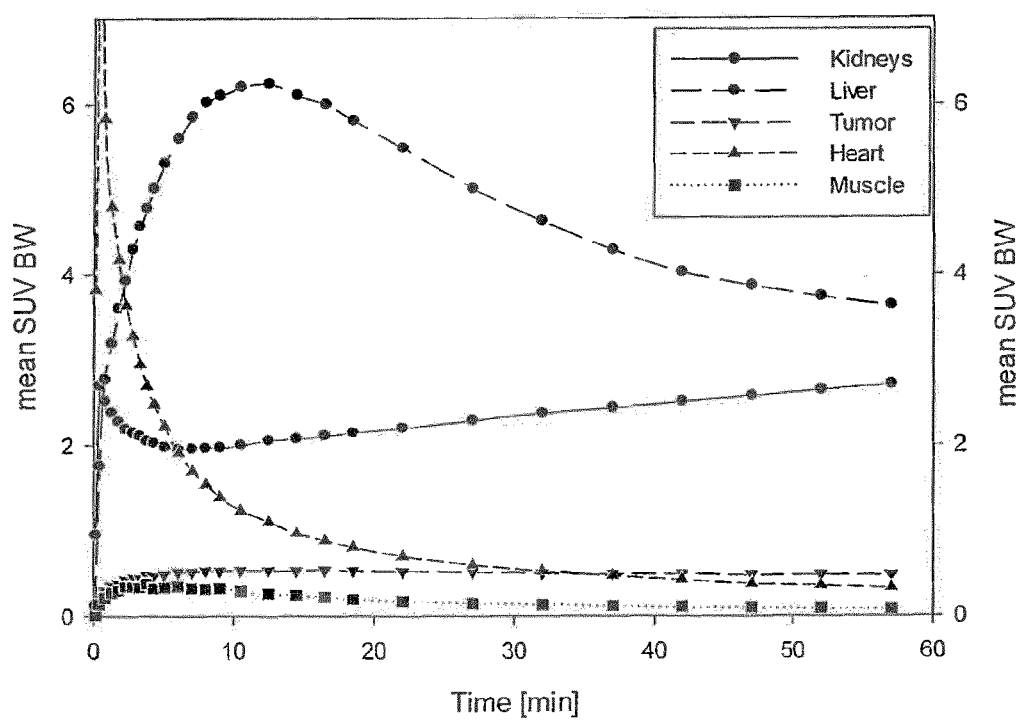
Figure 10:
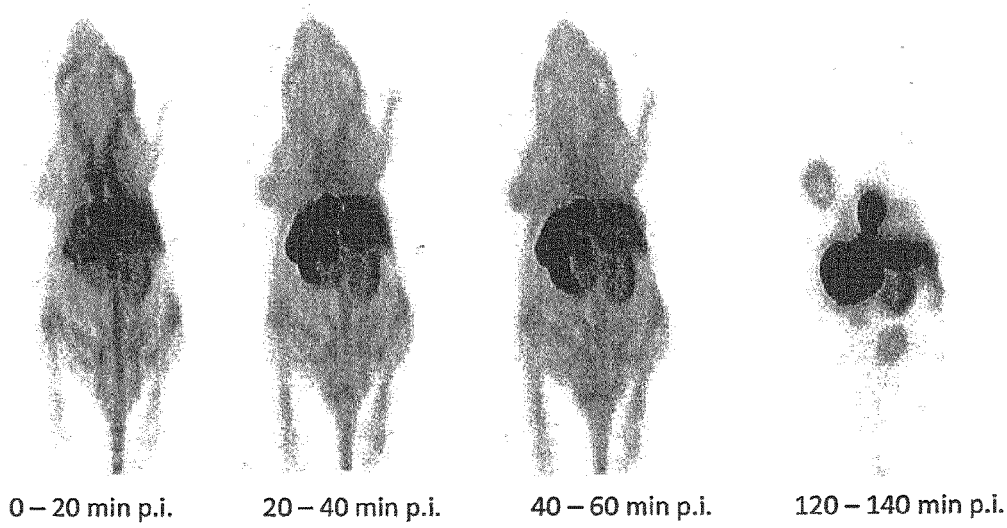
FIG. 10: PET imaging of PSMA-1003. Whole-body coronal microPET images of an athymic male nude mice bearing LNCaP tumor xenografts. The tumor-targeting efficacy and pharmacokinetic properties of $^{18}$F-PSMA-1003 were evaluated by dynamic microPET scans. Approximately 15 MBq/mouse were injected. The respective time-activity-curves of $^{18}$F-PSMA-1003 are shown in the lower part. The values are expressed as mean SUV (standardized uptake values).
Figure 10:
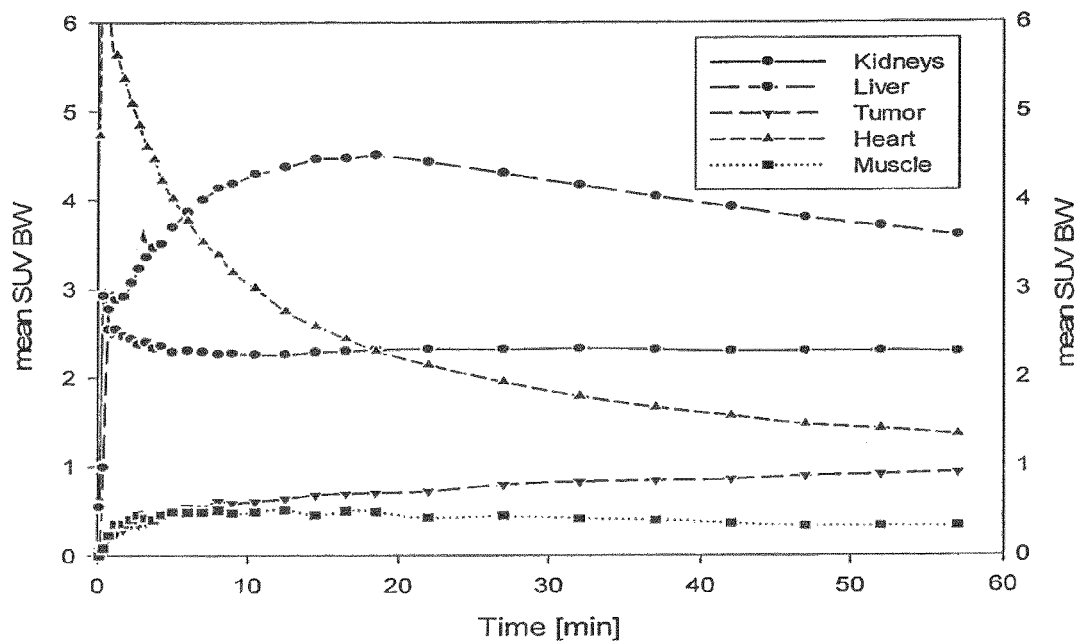

PSMA-1001 showed a high uptake in the liver, as well as an increasing uptake in the kidneys (FIG. 9). However, the compound also showed some uptake in the tumor, which was visualized with a standardized uptake value of 0.5 (FIG. 9). In a comparable experiment the application of PSMA-1003 showed even better results. While the uptake in the liver is still high, the uptake in the tumor is significantly better (SUV 0.9 at 57 minutes) and still increasing over time (FIG. 10). This finding is in good correlation with the internalization properties of the compounds. This is also reflected in the considerably better visualization of the tumor at 120 minutes (FIG. 10). Although further modification of the considered structures for improving the pharmacokinetic properties seem reasonable (e.g. reduction of the lipophilicity of the compounds), their capabilities have clearly been demonstrated by the results of the dynamic PET-experiment, in particular with PSMA-1003.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

The below example explains the invention in more detail but are not construed to limit the invention in any way to the exemplified embodiments only.

EXAMPLES

Example 1: Synthesis of $^{18}$F-Conjugated Inhibitors

The isocyanate of the glutamyl moiety was generated in situ by adding a mixture of 3 mmol of bis(tert-butyl) L-glutamate hydrochloride and 1.5 mL of N-ethyldiisopropylamine (DIPEA) in 200 mL of dry $CH_2Cl_2$ to a solution of 1 mmol triphosgene in 10 mL of dry $CH_2Cl_2$ at 0° C. over 4 h. After agitation of the reaction mixture for 1 h at 25° C., 0.5 mmol of the resin-immobilized (2-chloro-tritylresin) ε-allyloxycarbonyl protected lysine in 4 mL DCM was added and reacted for 16 h with gentle agitation. The resin was filtered off and the allyloxy-protecting group was removed using 30 mg tetrakis(triphenyl)palladium(0) and 400 µl morpholine in 4 mL $CH_2Cl_2$ for 3 hours.

The following coupling of 0-3 times 4-(Fmoc-aminomethyl)benzoic acid, Fmoc-3-(2-naphthyl)-L-alanine and 0-3 times trans-4-(Fmoc-aminomethyl)cyclohexanecarboxylic acid, respectively, was performed stepwise using 2 mmol of the Fmoc-protected acid, 1.96 mmol of HBTU and 2 mmol of N-ethyldiisopropylamine in a final volume of 4 mL DMF.

The product was cleaved from the resin in a 2 mL mixture consisting of trifluoroacetic acid, triisopropylsilane, and water (95:2.5:2.5). Purification was performed using RP-HPLC and the purified product was analysed by analytical RP-HPLC and MALDI-MS.

For the preparation of the non-radioactive reference compounds 50 mg of HBTU/DIPEA (0.98 and 1 Eq.) activated 6-Fluoronicotinic-3-acid was coupled in a final volume of 4 mL DMF and agitated for 1 h at room temperature and the product was the cleaved of the resin as described above.

In some preparations an $^{18}$F-tag reactive moieties (e.g. pent-4-ynoic acid or (Boc-aminooxy)acetic acid) were attached to the terminal amino-group for subsequent $^{18}$F labelling.

Radiosynthesis:
Preparation and Activation of the [$^{18}$F]Fluoride

Fluorine-18 was produced by the irradiation of 180-enriched water with 16.5 MeV protons using the $^{18}O(p,n)^{18}F$ nuclear reaction. Irradiations were performed with the Scanditronix MC32NI cyclotron at the department of Radiopharmaceutical Chemistry (E030) at the German Cancer Research Center Heidelberg.

After transfer of the irradiated water to an automated system (Trasis All In One 32) the [$^{18}$F]F$^-$ was separated from the [$^{18}$O]H$_2$O by passing through an previously conditioned (5 mL 1 M $K_2CO_3$ and 10 mL water) anion exchange cartridge (Waters Accel™ Plus QMA Cartridge light) and subsequently eluted with a 2 mL acetonitrile containing 20 mg of the aminopolyether Kryptofix® 2.2.2 in 28 µl 1 M $K_2CO_3$. The mixture was evaporated to dryness at 80° C. under a stream of nitrogen. This azeotropic distillation was subsequently repeated two times by adding 1.8 mL of dry acetonitrile for each step. Then the dry residue was dissolved in 2.5 mL of dry acetonitrile and this mixture was used for the labelling reactions.

In an alternative approach, after transfer of the irradiated water to an automated system (Trasis All In One 32) the [$^{18}$F]F$^-$ was separated from the [$^{18}$O]H$_2$O by passing through a previously conditioned (5 mL 1 M $K_2CO_3$ and 10 mL water) anion exchange cartridge (Waters Accel™ Plus QMA Cartridge light) and subsequently eluted with a mixture of 800 µl acetonitrile and 150 µl tetrabutylammonium bicarbonate solution (320 mM in water). The mixture was evaporated to dryness at a temperature of 100° C. under a stream of nitrogen. This distillation was subsequently repeated two times by adding 1.8 mL of acetonitrile for each step. After applying maximum achievable vacuum to the residue for 5 minutes at 100° C. and subsequent cooling to 50° C. the dry residue was dissolved in 2 mL of tert-butanol/acetonitrile (8:2) and used for the labelling reactions.

In a further alternative, the n.c.a. [$^{18}$F]fluoride was dried and activated by azeotropic distillation in presence of 150 µl tetrabutylammonium bicarbonate solution (320 mM in water) as base in an All in One module (Trasis) by an automated procedure. The [$^{18}$F]fluoride was then dissolved in 2 mL of tert-butanol/acetonitrile (8:2) and used for labelling reactions.

6-[$^{18}$F]Fluoronicotinic Acid Tetrafluorophanyl Ester

To 10 mg N,N,N-Trimethyl-5-((2,3,5,6-tetrafluorophenoxy)-carbonyl)pyridin-2-aminium trifluoromethanesulfonate 1 mL of tert-butanol/Acetonitrile (8:2) containing the dried [$^{18}$F]KF-Kryptofix 2.2.2 komplex (2-20 MBq $^{18}$F) was added and the mixture was heated at 40° C. After 10 minutes the mixture was diluted with 3 mL of water and the product loaded on a preconditioned Oasis MCX Plus Sep-Pak (Waters). The cartridge was rinsed with 5 mL of water and the purified 6-[$^{18}$F]Fluoronicotinic acid tetrafluorophanyl ester was eluted back to the reaction vessel using 2 mL of water/acetonitrile (7:13).

Peptide Conjugation

The peptide conjugation was accomplished by adding 2 mg of the desired peptide in 1 mL of a 1:1 mixture of DMSO/Buffer (0.2 M phosphate buffer, pH 8.0) to the crude 6-[$^{18}$F]Fluoronicotinic acid tetrafluorophanyl ester and subsequent heating of the mixture at 40° C. for 10 minutes. The products were analyzed by radio-HPLC and comparison of the retention times with the respective non-radioactive reference compounds.

Example 2: Labelling Compounds PSMA-1001, PSMA-1002, PSMA-1003 and PSMA-1005

The labeling compounds PSMA-1001, PSMA-1002 and PSMA-1003 and their precursors were prepared according to the general method as described above.

Precursors (P):

PSMA-1001-P: (Glu)-(Urea)-(Lys)-(2-Nal)-(Chx)-NH$^2$ ($C_{33}H_{45}N_5O_9$, 655.74 g/mol)

MS (MALDI): m/z=656.3 [M+H$^+$]$^+$, 678.3 [M+Na$^+$]$^+$

PSMA-1002-P: (Glu)-(Urea)-(Lys)-(2-Nal)-NH$_2$ ($C_{25}H_{32}N_4O_8$, 516.54 g/mol)

MS (MALDI): m/z=517.1 [M+H$^+$]$^+$, 539.1 [M+Na$^+$]$^+$

PSMA-1003-P: (Glu)-(Urea)-(Lys)-(2-Nal)-(Bn)-NH$^2$ ($C_{33}H_{39}N_4O_9$, 649.49 g/mol)

MS (MALDI): m/z=650.3 [M+H$^+$]$^+$, 672.3 [M+Na$^+$]$^+$

PSMA-1005-P: (Glu)-(Urea)-(Lys)-(2Nal)-(Bn)-(COCH$_2$ONH$_2$)($C_{35}H_{42}N_6O_{11}$, 722.74 g/mol)

MS (MALDI): m/z=722.7 [M+Na$^+$]$^+$ $^{18}$F-PSMA-1001:

(Glu)-(Urea)-((D)-Lys)-(2-Naphthylalanine)-(4-(Aminomethyl)cyclohexanecarboxylic acid)-FN ($C_{39}H_{41}FN_6O_{10}$, 778.823 g/mol)

MS (MALDI): m/z=779.7 [M+H$^+$]$^+$, 801.7 [M+Na$^+$]$^+$

PSMA-1001

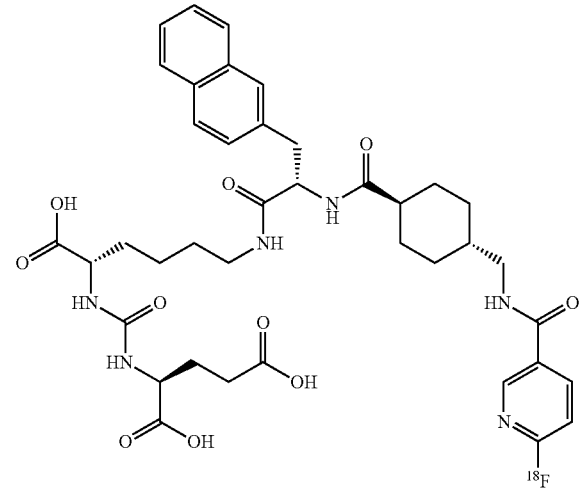

RCA: 30-45%

HPLC (Gradient: 5:95-5:95 Acetonitrile/0.1% aqueous TFA in 12.5 min; Flow: 3 mL/min; Column: Merck Chromolith® Performance RP-18e 100-4.6 mm): t$_{ret}$: 5.02 min (t$_{dead}$: 0.56 min)

$^{18}$F-PSMA-1002: (Glu)-(Urea)-((D)-Lys)-(2-Naphthylalanine)-FN ($C_{31}H_{34}FN_5O_9$, 639.63 g/mol)

MS (MALDI): m/z=640.4 [M+H$^+$]$^+$, 662.4 [M+Na$^+$]$^+$

PSMA 1002

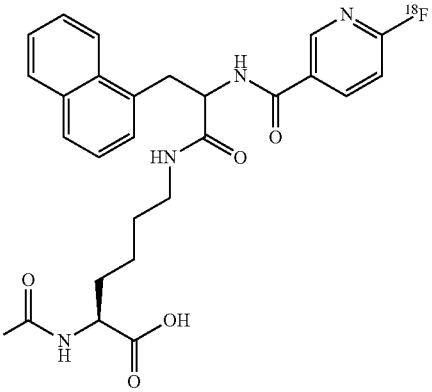

RCA: 20-30%

HPLC (Gradient: 5:95-5:95 Acetonitrile/0.1% aqueous TFA in 12.5 min; Flow: 3 mL/min; Column: Merck Chromolith® Performance RP-18e 100-4.6 mm): t$_{ret}$: 4.79 min (t$_{dead}$: 0.56 min)

$^{18}$F-PSMA-1003: (Glu)-(Urea)-((D)-Lys)-(2-Naphthylalanine)-(4-(Aminomethyl)benzoic acid)-FN ($C_{39}H_{41}FN_6O_{10}$, 772.78 g/mol)

MS (MALDI): m/z=773.3 [M+H$^+$]$^+$, 795.4 [M+Na$^+$]$^+$

RCA: 45-60%

HPLC (Gradient: 5:95-5:95 Acetonitrile/0.1% aqueous TFA in 12.5 min; Flow: 3 mL/min; Column: Merck Chromolith® Performance RP-18e 100-4.6 mm): t$_{ret}$: 5.09 min (t$_{dead}$: 0.56 min)

$^{18}$F-PSMA-1005: (Glu)-(Urea)-(Lys)-(2Nal)-(Bn)-(Acetyl-FDG-Oxim) ($C_{41}H_{51}FN_6O_{15}$, 886.87 g/mol)

700 µg PSMA-1005-precursor were dissolved in 20 µl Ethanol in a 500 µl reaction vial. Subsequently 1.5 mg FOG in 100 µl H$_2$O containing 0.9% NaCl and 0.4% TFA were added and the resulting solution heated at 100° C. for 30 minutes. The products (E- and Z-isomere) were separated by means of HPLC and dried by lyophilization.

10 µl of a PSMA-1005-P solution (10 mg/ml) were reacted with 40 µl [$^{18}$F]FDG solution containing 100-200 MBq activity (residual solution from the routine production for the clinic; solution according to the quality criteria from the EU-Pharmacopaia) in a 500 µl reaction vial at 100° C. for 30 minutes. The products (E- and Z-form) were separated by HPLC.

RCA: ca. 1%

HPLC (Gradient: 5:95-5:95 Acetonitrile/0.1% aqueous TFA in 12.5 min; Flow: 3 mL/min; Column: Merck Chromolith® Performance RP-18e 100-4.6 mm): t$_{ret}$: 3.89/3.95 min (E- and Z-form) (t$_{dead}$: 0.56 min)

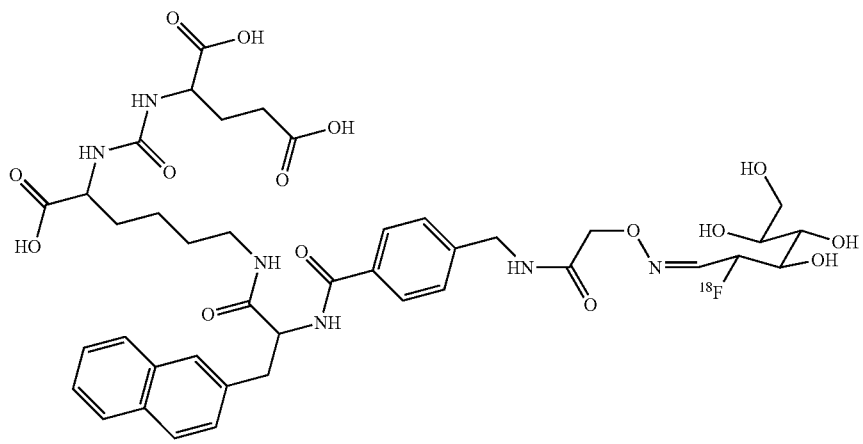 [SMILES: O=C(O)CCC(NC(=O)NC(CCCCNC(=O)C(Cc1ccc2ccccc2c1)NC(=O)c1ccc(CNC(=O)CO/N=C\C([18F])C(O)C(O)C(O)CO)cc1)C(=O)O)C(=O)O]

MS (MALDI): m/z=887.1 [M+H+]+

Cell Culture

For binding studies and in vivo experiments LNCaP cells (metastatic lesion of human prostatic adenocarcinoma, ATCC CRL-1740) were cultured in RPMI medium supplemented with 10% fetal calf serum and Glutamax (PAA, Austria). During cell culture, cells were grown at 37° C. in an incubator with humidified air, equilibrated with 5% CO2. The cells were harvested using trypsin-ethylenediaminetetraacetic acid (trypsin-EDTA; 0.25% trypsin, 0.02% EDTA, all from PAA, Austria) and washed with PBS.

Cell Binding and Internalization

The competitive cell binding assay and internalization experiments were performed as described previously (Eder, M. et al., Bioconj. Chem 2012, 23, 688-697) Briefly, the respective cells ($10^5$ per well) were incubated with the radioligand ($^{68}$Ga-labeled [Glu-urea-lys(Ahx)]2-HBED-CC (Schafer, M. et al., EJNMMI Res. 2012; 2, 23) in the presence of 12 different concentrations of analyte (0-5000 nM, 100 µL/well). After incubation, washing was carried out using a multiscreen vacuum manifold (Millipore, Billerica, Mass.). Cell-bound radioactivity was measured using a gamma counter (Packard Cobra II, GMI, Minnesota, USA). The 50% inhibitory concentration ($IC^{50}$) was calculated by fitting the data using a nonlinear regression algorithm (GraphPad Software).

Experiments were performed three times. Reference is made to Table A below.

To determine the specific cell uptake and internalization, $10^5$ cells were seeded in poly-L-lysine coated 24-well cell culture plates 24 h before incubation. After washing, the cells were incubated with 30 nM of the radiolabeled compounds for 45 min at 37° C. Specific cellular uptake was determined by competitive blocking with 2-(phosphonomethyl)pentanedioic acid (500 µM final concentration, PMPA, Axxora, Loerrach, Germany). Cellular uptake was terminated by washing 3 times with 1 mL of ice-cold PBS. Cells were subsequently incubated twice with 0.5 mL glycine-HCl in PBS (50 mM, pH=2.8) for 5 min to remove the surface-bound fraction. The cells were washed with 1 mL of ice-cold PBS and lysed using 0.3 N NaOH (0.5 mL). The surface-bound and the internalized fractions were measured in a gamma counter. The cell uptake was calculated as percent of the initially added radioactivity bound to $10^5$ cells [% ID/$10^5$ cells]. The main results are given in Table B below and in FIG. 8.

TABLE A

Binding Affinity Assay

| Compound | IC$_{50}$ [nM] |
| --- | --- |
| PSMA-1001 | 3 |
| PSMA-1002 | 3 |
| PSMA-1003 | 3 |
| PSMA-1005 | 7 |

TABLE B

Internalization

| Compound | Cell surface [% ID/$10^5$ cells] | Internalised [% ID/$10^5$ cells] | Internalized fraction [%]* |
| --- | --- | --- | --- |
| PSMA-1001 | 8.4 ± 1.9 | 2.9 ± 0.3 | 26 |
| PSMA-1002 | 9.4 ± 1.1 | 2.8 ± 0.5 | 23 |
| PSMA-1003 | 11.7 ± 1.2 | 7.1 ± 0.8 | 38 |
| PSMA-1005 | 1.1 ± 0.5 | 0.7 ± 0.4 | 63 |

*(Internalized activity/total activity)*100
ID = Injected Dose = Injected Activity (IA)

In Vivo Experiments

For in vivo experiments, 8 week old BALB/c nu/nu mice were subcutaneously inoculated into the right trunk with 5×$10^6$ LNCaP- or PC3-cells in 50% Matrigel. When the size of tumor was approximately 1 cm$^3$, the radiolabeled compound was injected via the tail vein (ca. 30 MBq, 60 pmol for µPET imaging; ca. 1 MBq, 60 pmol for organ distribution).

Organ Distribution

The F-18 labeled compounds were injected via tail vein (1-2 MBq per mouse; 60 pmol). At 1 h after injection, the animals were sacrificed. Organs of interest were dissected, blotted dry, and weighed. The radioactivity was measured with a gamma counter (Packard Cobra II, GMI, Minnesota, USA) and calculated as % ID/g.

TABLE C

Organ distribution of $^{18}$F-PSMA-1003

| Organ | Mean [% ID/g] | SD [% ID/g] | n |
| --- | --- | --- | --- |
| Blood | 2.02 | 2.65 | 3 |
| Heart | 0.25 | 0.01 | 3 |
| Lung | 0.65 | 0.04 | 3 |

TABLE C-continued

Organ distribution of $^{18}$F-PSMA-1003

| Organ | Mean [% ID/g] | SD [% ID/g] | n |
|---|---|---|---|
| Spleen | 1.96 | 0.08 | 3 |
| Liver | 3.02 | 1.31 | 3 |
| Kidney | 32.37 | 2.91 | 3 |
| Muscle | 0.25 | 0.04 | 3 |
| Small intestine | 8.49 | 5.17 | 3 |
| Brain | 0.07 | 0.01 | 3 |
| LNCaP Tumor | 3.4 | 0.59 | 3 |

MicroPET

For the microPET studies, 10-25 MBq of the radiolabeled compounds in a volume of 0.15 mL (~60 pmol) were injected via a lateral tail vein into mice bearing LNCaP tumor xenografts. The anesthetized animals (2% sevoflurane, Abbott, Wiesbaden, Germany) were placed in prone position into the Inveon small animal PET scanner (Siemens, Knoxville, Tenn., USA) to perform dynamic micro-PET scans and 20 min-static scans. The results are shown in FIGS. 9 and 10.

Plasma Binding

For the determination of the plasma binding 3 µl of 6 µmolar c.a. [$^{18}$F]PSMA solution was added to 300 µl human serum AB and incubated at 37° C. for 1 h. Subsequently the product mixture was analyzed by size-exclusion chromatography.

No plasma binding was observed with any of the compounds.

Plasma Stability

For the determination of the plasma stability 50 µl of 6 µmolar c.a. [$^{18}$F]PSMA solution was added to 450 µl human serum AB and incubated at 37° C. At 1, 2 and 4 h samples were prepared. Therefore 100 µl of the tracer/plasma mixture were added to 100 µl of acetonitrile. Subsequently the mixture was centrifuged at 13000 rpm for 3 minutes. 100 µl of the supernatant were added to 100 µl of acetonitrile, centrifuged at 13000 rpm for 5 minutes, the liquid separated from any residual solids and analyzed by HPLC.

All of the compounds were stable in human plasma at 37° C. for at least 4 hours

All compounds were labelled with fluorine-18 via 2-[$^{18}$F] fluoronicotinic acid TFP ester in good radiochemical yields. Table A shows that the binding affinity of the PSMA inhibitors prepared so far are essentially the same and in the typical range. Further, all compounds were specifically internalized at 37° C. with rather high cellular uptake and internalization values (Table B and FIG. 8). Former studies demonstrated that this is due to the aromatic moieties in the linker region and that besides binding affinity the internalization properties of PSMA-targeting probes are essential for the in vivo tumor uptake and retention. Thus the compounds investigated exhibit optimal in vitro characteristics for a high contrast PET imaging. Two of the compounds, namely PSMA-1001 and PSMA-1003, were further evaluated by micro-PET. The results are summarized in FIGS. 9 and 10, respectively.

PSMA-1001 showed a high uptake in the liver, as well as an increasing uptake in the kidneys (FIG. 9). However, the compound also showed some uptake in the tumor, which was visualized with a standardized uptake value$_{(SUVmean,BW)}$ of 0.5 (FIG. 9). In a comparable experiment the application of PSMA-1003 showed even better results. While the uptake in the liver is still high, the uptake in the tumor is significantly better (SUV 0.9 at 57 minutes) and still increasing over time (FIG. 10). This finding is in good correlation with the internalization properties of the compounds. This is also reflected in the considerably better visualization of the tumor at 120 minutes (FIG. 10). For the compound PSMA-1003 this has further been demonstrated by organ distribution experiments. In those experiments the compound showed a tumor uptake of 3.4% ID/g (at 60 min p.i.). Besides, the compounds also showed some uptake in excretion organs, such as the liver (3.0% ID/g) and the small intestines (8.5% ID/g) as well as an uptake in the kidneys (32.4%10/g). The uptake in the kidneys is typical for PSMA targeting substances and known to be specific. Although further modification of the considered structures for improving the pharmacokinetic properties seem reasonable (e.g. reduction of the lipophilicity of the compounds), their capabilities have clearly been demonstrated by the results of the dynamic PET-experiment and the organ distribution experiments with PSMA-1003.

Further experiments were conducted with [$^{18}$F]FDG as prosthetic group, coupled via an oxime-linker. Due to the small radiochemical yield of about 1% (not optimized) the products were not separated from each other. The products showed only a small decrease in affinity (IC$_{50}$ 7 nM against $^{68}$Ga-PSMA-10) while the internalized fraction was very high (63%). Thus, we demonstrated clearly, that an exchange of the aromatic prosthetic group 6-[$^{18}$F]fluoronicotinic acid by aliphatic prosthetic groups is possible. With respect to the internalization this even seems to be beneficial—at least in the case of FDG.

The invention is further described by the following numbered paragraphs:

1. A compound of formula (Ia) or (Ib):

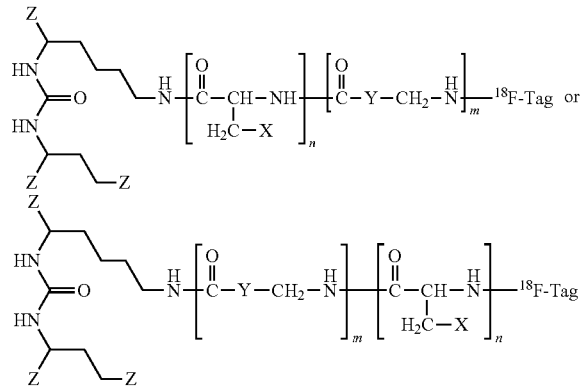

with:

| | |
|---|---|
| n: | 0, 1 |
| m: | 0, 1, 2, 3, 4 with proviso that m + n > 0 |
| Z: | —CO$_2$H, —SO$_2$H, —SO$_3$H, —SO$_4$H, —PO$_2$H, —PO$_3$H, —PO$_4$H$_2$ |
| X: | Naphthyl, Phenyl, Biphenyl, Indolyl (=2,3-benzopyrrolyl), Benzothiazolyl |
| Y: | Aryl, Alkylaryl, Cyclopentyl, Cyclohexyl, Cycloheptyl |

$^{18}$F-Tag:

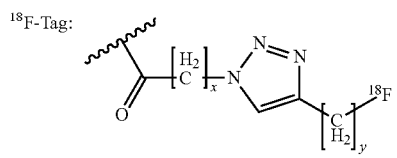

x = 1-5 y = 1-5

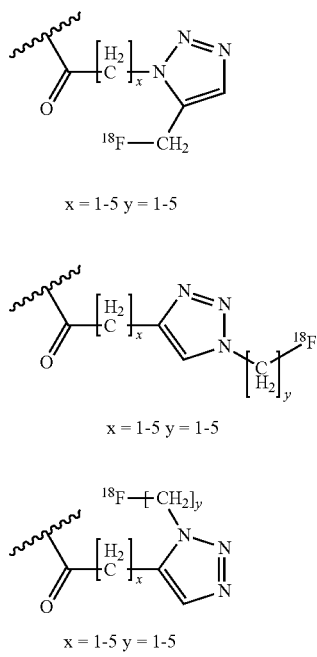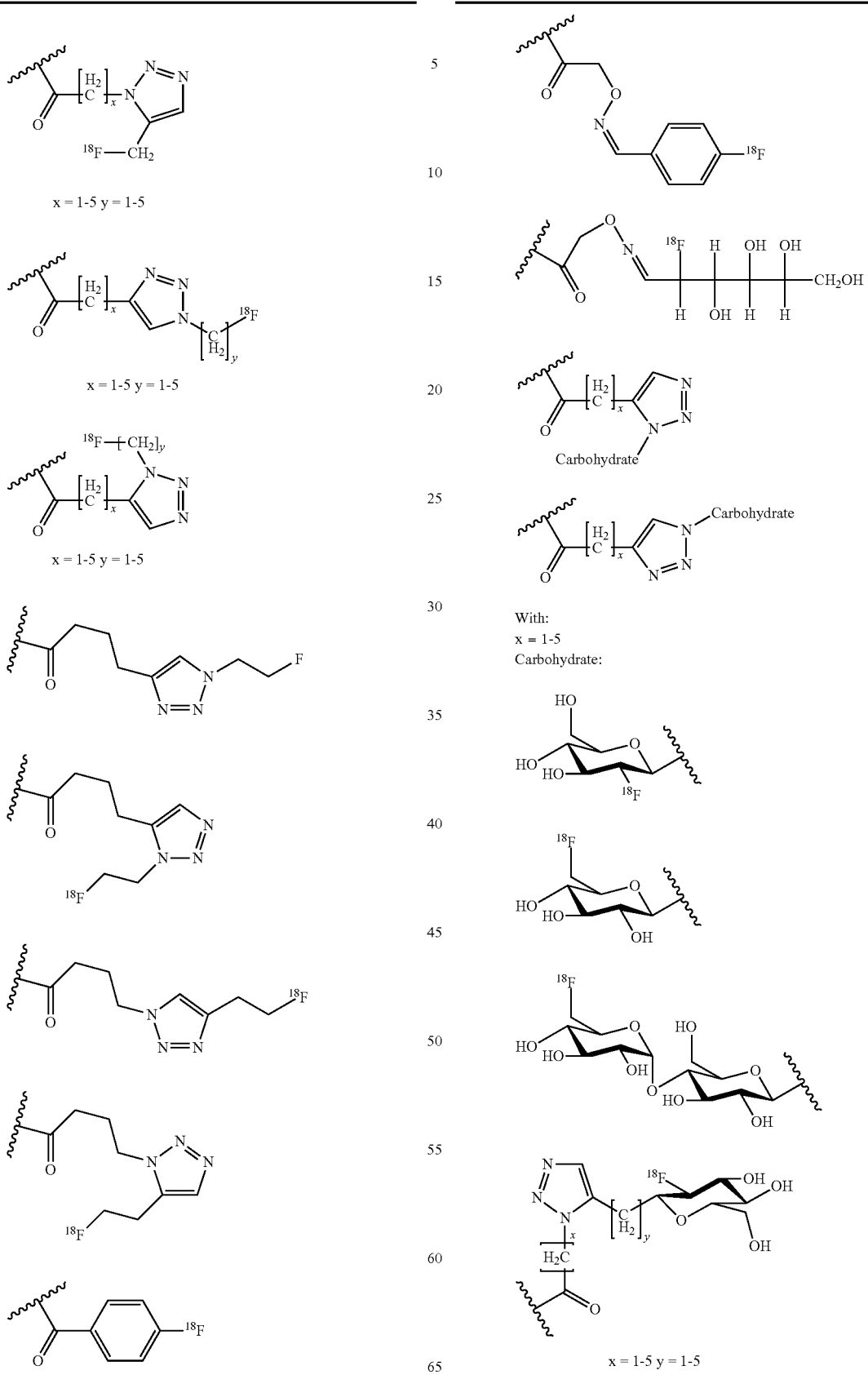

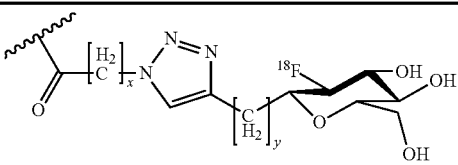

x = 1-5 y = 1-5

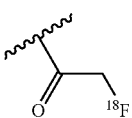 [SMILES: *C(=O)C[18F]]

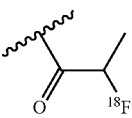

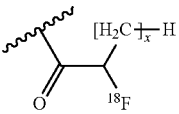

x = 1-10

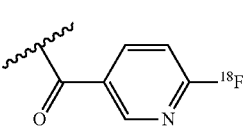 [SMILES: *C(=O)c1ccc([18F])nc1]

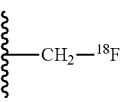

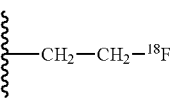

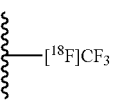

x = 1-10

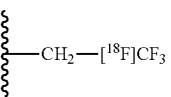

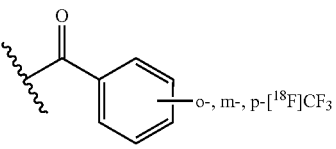

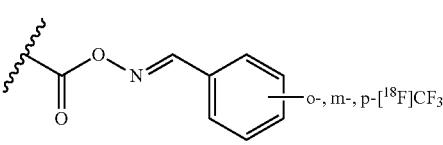

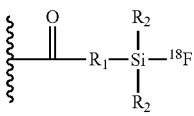

$R_1$: Any alkyl, aryl or arylalkyl linker
especially methyl, 2-ethyl, 3-propyl,
2-, 3-, 4-phenyl, 2-, 3-, 4-phenylmethyl, 2-, 3-, 4-phenylpropyl
$R_2$: Any alkyl or aryl group
especially methyl isopropyl, tert-butyl,
phenyl or 1-naphtyl

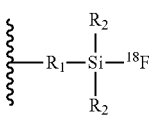

$R_1$: Any alkyl, aryl or arylalkyl linker
especially methyl, 2-ethyl, 3-propyl,
2-, 3-, 4-phenyl, 2-, 3-, 4-phenylmethyl, 2-, 3-, 4-phenylpropyl
$R_2$: Any alkyl or aryl group
especially methyl isopropyl, tert-butyl,
phenyl or 1-naphtyl

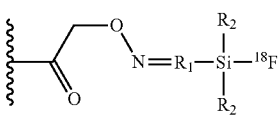

$R_1$: Any alkyl, aryl or arylalkyl linker
especially methyl, 2-ethyl, 3-propyl,
2-, 3-, 4-phenyl, 2-, 3-, 4-phenylmethyl, 2-, 3-, 4-phenylpropyl
$R_2$: Any alkyl or aryl group
especially methyl isopropyl, tert-butyl,
phenyl or 1-naphtyl

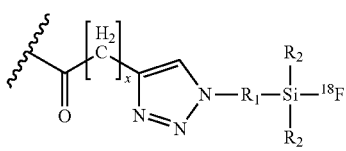

x = 1-5

$R_1$: Any alkyl, aryl or arylalkyl linker
especially methyl, 2-ethyl, 3-propyl,
2-, 3-, 4-phenyl, 2-, 3-, 4-phenylmethyl, 2-, 3-, 4-phenylpropyl
$R_2$: Any alkyl or aryl group
especially methyl isopropyl, tert-butyl,
phenyl or 1-naphtyl

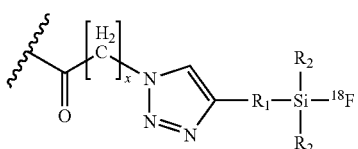

x = 1-5

$R_1$: Any alkyl, aryl or arylalkyl linker
especially methyl, 2-ethyl, 3-propyl,
2-, 3-, 4-phenyl, 2-, 3-, 4-phenylmethyl, 2-, 3-, 4-phenylpropyl
$R_2$: Any alkyl or aryl group
especially methyl isopropyl, tert-butyl,
phenyl or 1-naphtyl

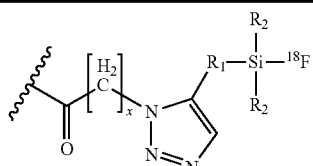

x = 1-5

$R_1$: Any alkyl, aryl or arylalkyl linker
especially methyl, 2-ethyl, 3-propyl,
2-, 3-, 4-phenyl, 2-, 3-, 4-phenylmethyl, 2-, 3-, 4-phenylpropyl
$R_2$: Any alkyl or aryl group
especially methyl isopropyl, tert-butyl,
phenyl or 1-naphtyl

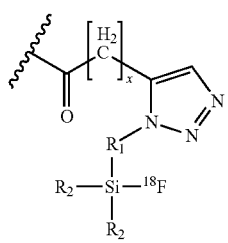

x = 1-5

$R_1$: Any alkyl, aryl or arylalkyl linker
especially methyl, 2-ethyl, 3-propyl,
2-, 3-, 4-phenyl, 2-, 3-, 4-phenylmethyl, 2-, 3-, 4-phenylpropyl
$R_2$: Any alkyl or aryl group
especially methyl isopropyl, tert-butyl,
phenyl or 1-naphtyl.

2. The compound of paragraph 1 having the structure R'-Linker-R with R'=$^{18}$F-Tag and R=Glu-Urea-Lys:

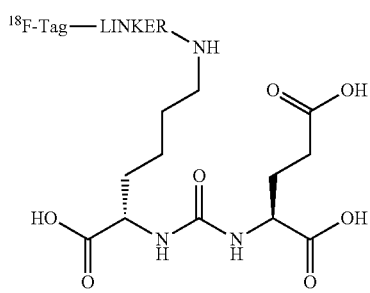

wherein the linker is selected from the group

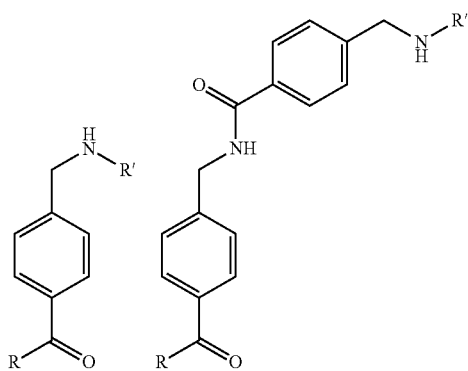

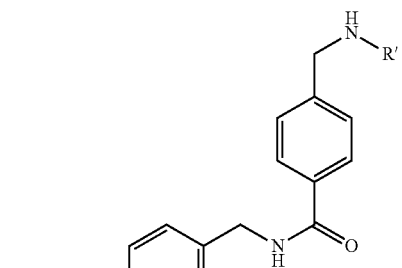

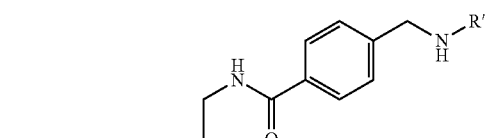

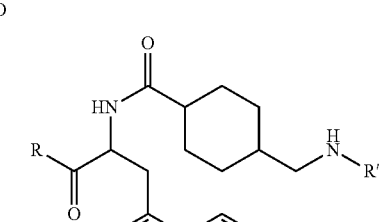

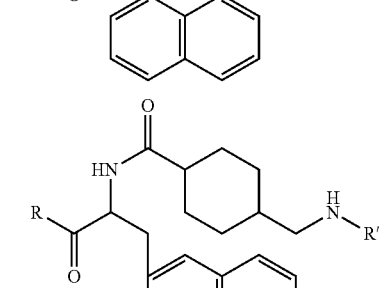

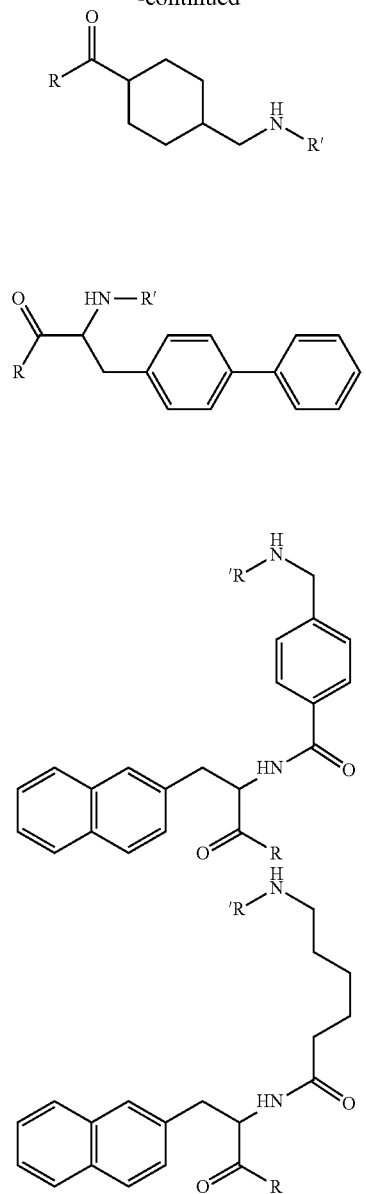
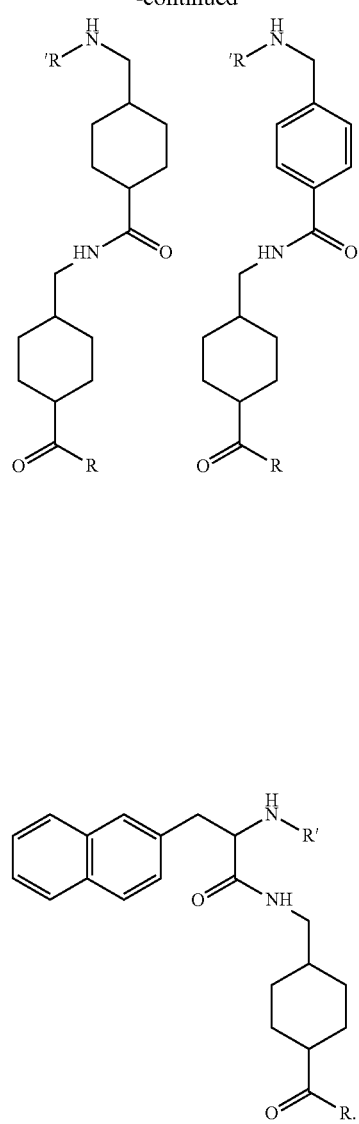
3. The compound of paragraph 1 or 2, selected from the following:
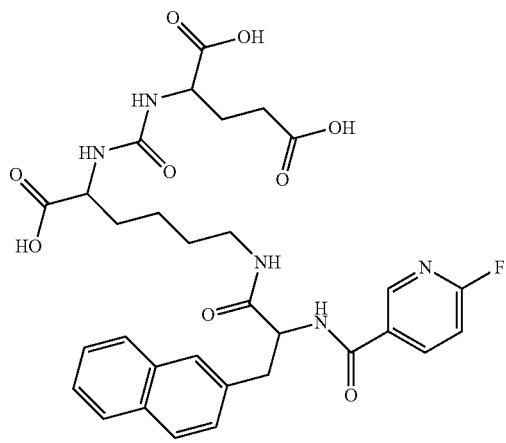
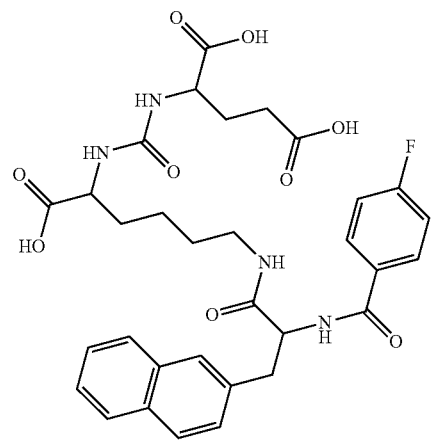

49
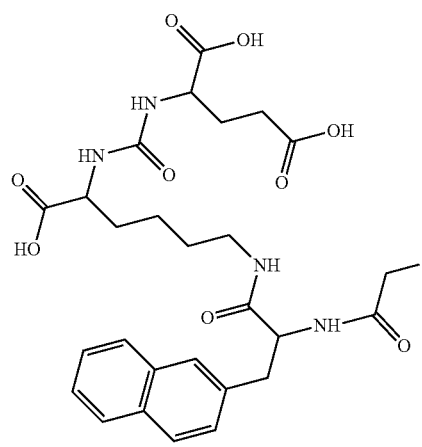
50
-continued
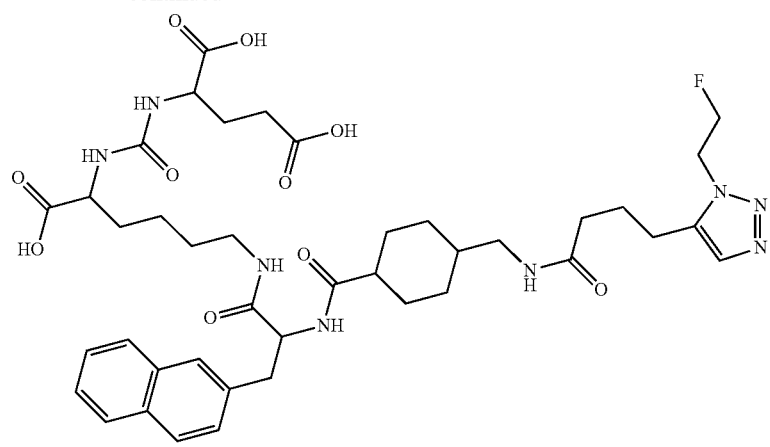
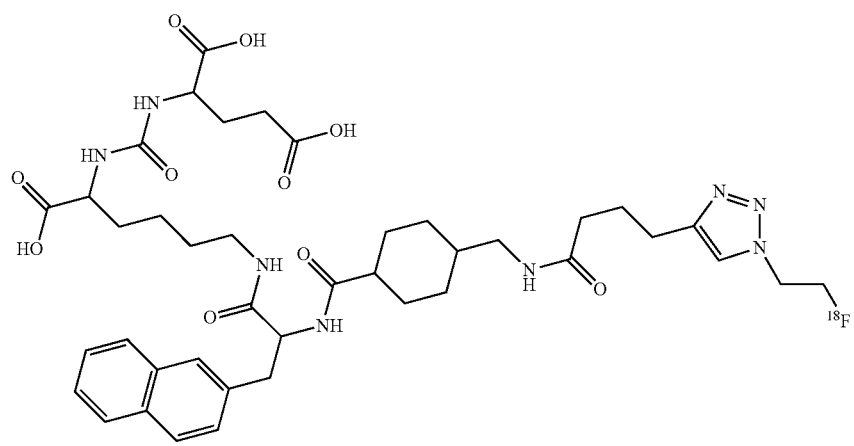
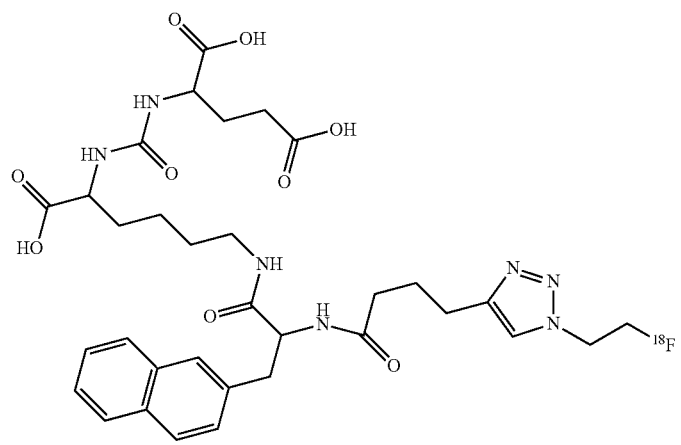

-continued
51
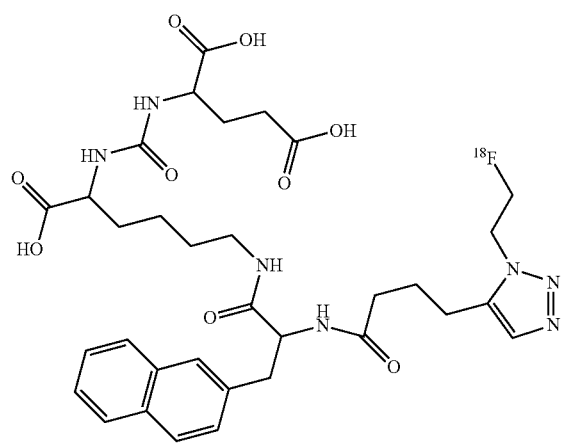
52
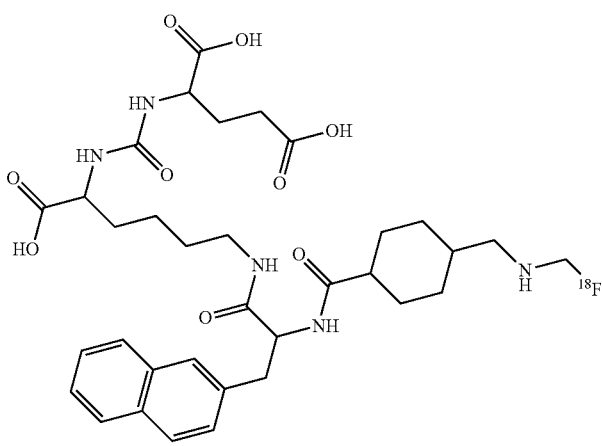
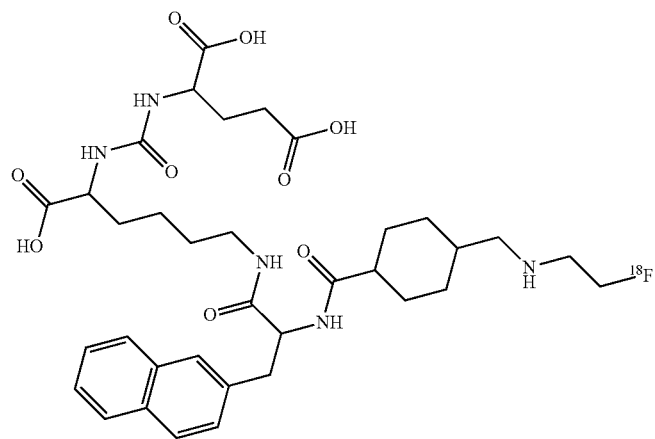
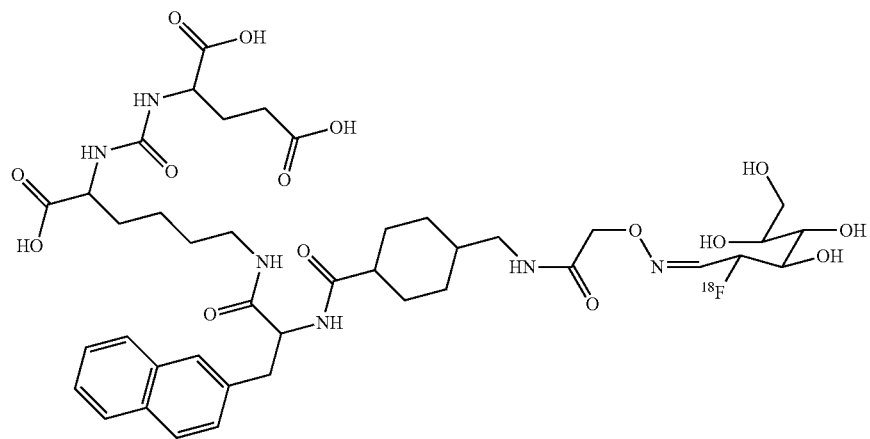

-continued

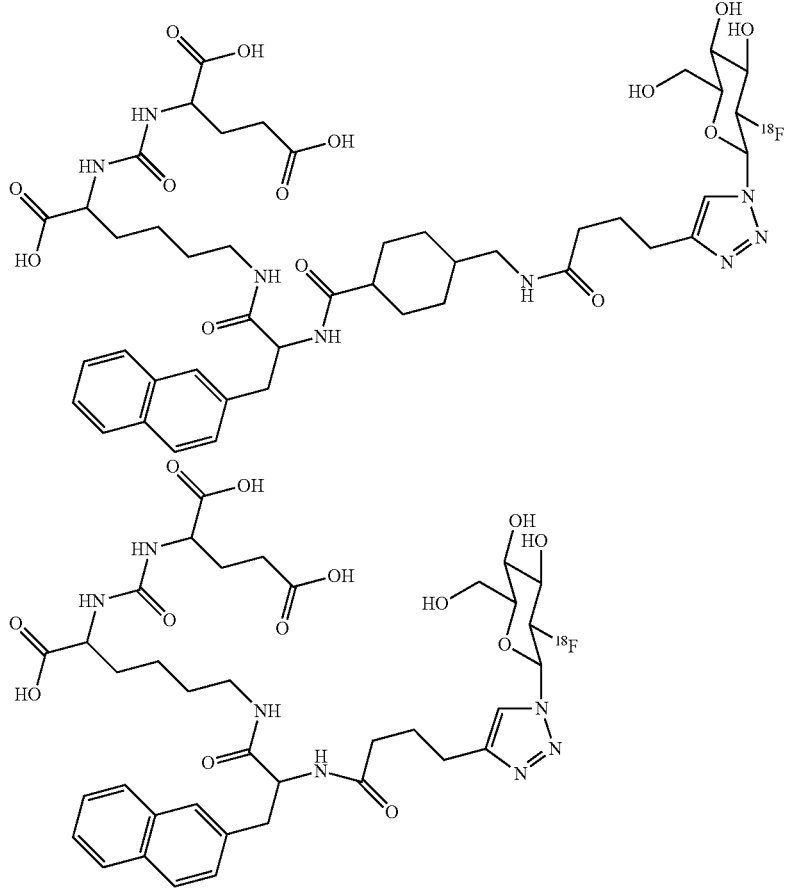

4. A pharmaceutical composition comprising a compounded of any paragraphs 1 to 3, or a pharmaceutically acceptable salt, or ester thereof, and a pharmaceutically acceptable carrier.

5. Compound of any of paragraphs 1 to 3 for use in a method of imaging in a patient.

6. Compound of any paragraphs 1 to 3 for use in a method of diagnosing prostate cancer and/or metastasis thereof.

7. Compound of any of paragraphs 1 to 3 for use in a method of treating prostate cancer and/or metastasis thereof.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A compound of formula (Ia) or (Ib):

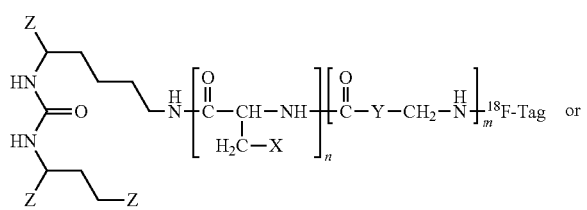

-continued

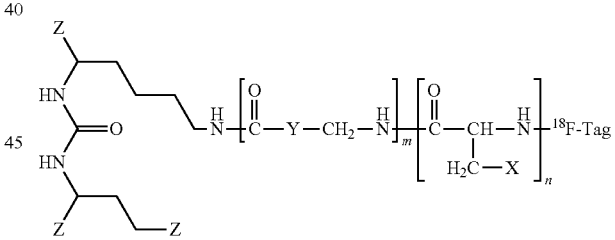

with:

n is 0 or 1;
m is 0, 1, 2, 3 or 4, with the proviso that m + n > 0;
Z is —$CO_2H$, —$SO_2H$, —$SO_3H$, —$SO_4H$, —$PO_2H$, or —$PO_4H_2$;
X is naphthyl, phenyl, biphenyl, indolyl (=2,3-benzopyrrolyl), or benzothiazolyl;
Y is aryl, alkylaryl, cyclopentyl, cyclohexyl, or cycloheptyl; and
$^{18}F$-Tag is

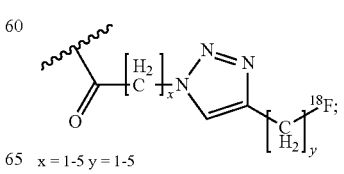

x = 1-5 y = 1-5

55
-continued
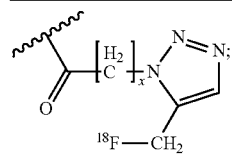
x = 1-5 y = 1-5
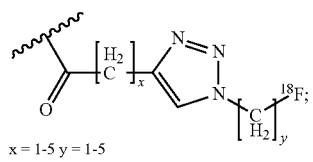
x = 1-5 y = 1-5
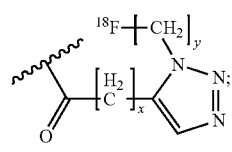
x = 1-5 y = 1-5
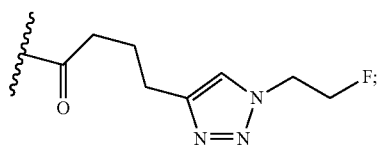 [SMILES: *C(=O)CCCc1cn(CCF)nn1]
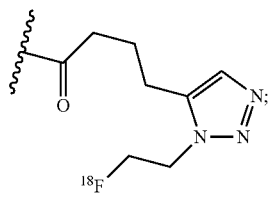 [SMILES: *C(=O)CCCc1cnnn1CC[18F]]
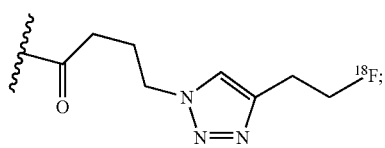
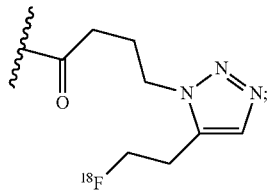 [SMILES: *C(=O)CCCn1nncc1CC[18F]]
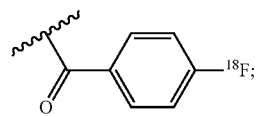
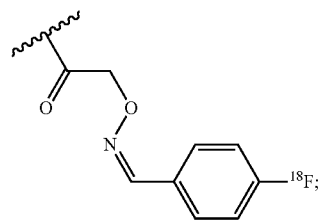
56
-continued
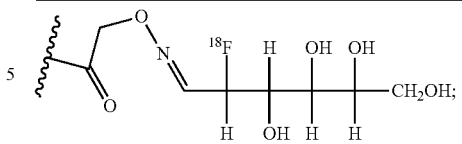
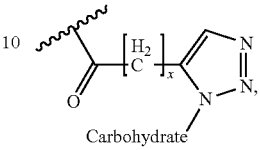
With:
x = 1-5
wherein the carbohydrate is
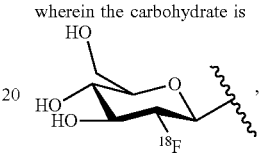,
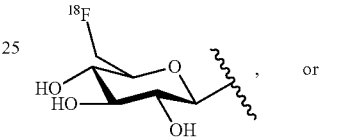, or
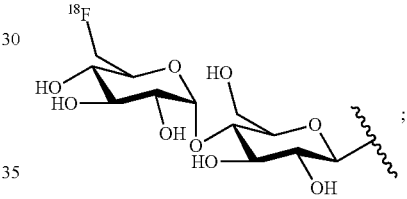;
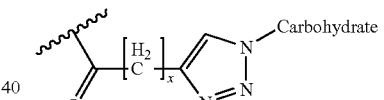
With:
x = 1-5
wherein the carbohydrate is
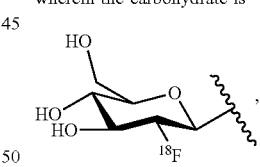,
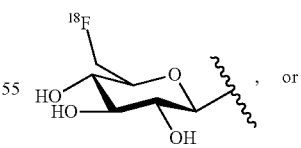, or
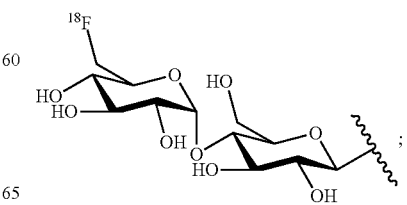;

-continued

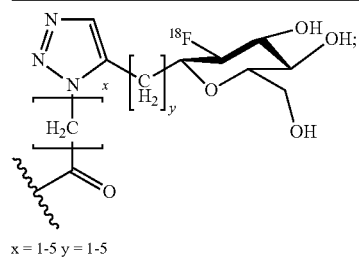

x = 1-5 y = 1-5

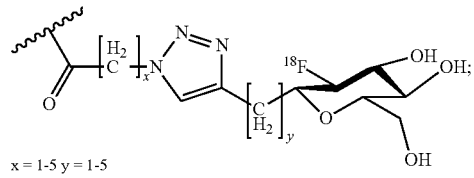

x = 1-5 y = 1-5

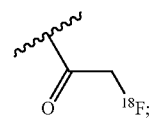

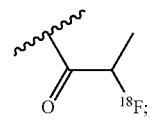

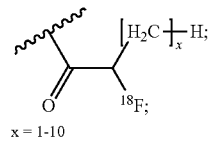

x = 1-10

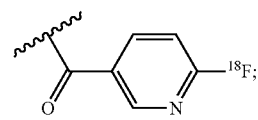

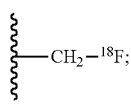

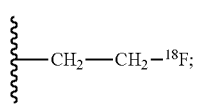

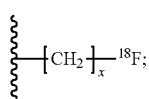

x = 1-10

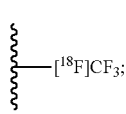

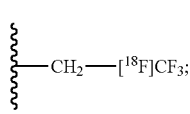

-continued

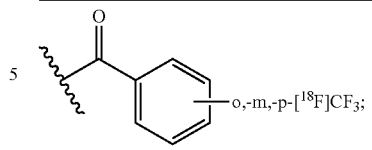

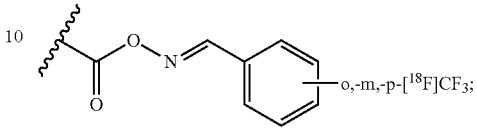

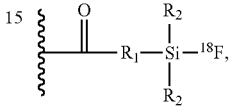

$R_1$: Any alkyl, aryl or arylalkyl linker and
$R_2$: Any alkyl or aryl group;

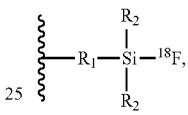

$R_1$: Any alkyl, aryl or arylalkyl linker and
$R_2$: Any alkyl or aryl group;

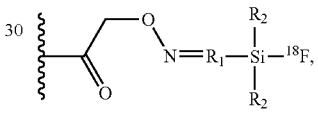

$R_1$: Any alkyl, aryl or arylalkyl linker and
$R_2$: Any alkyl or aryl group;

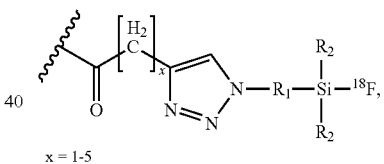

x = 1-5

$R_1$: Any alkyl, aryl or arylalkyl linker and
$R_2$: Any alkyl or aryl group;

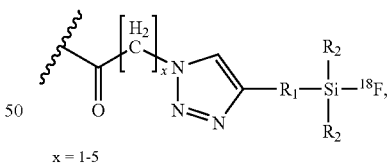

x = 1-5

$R_1$: Any alkyl, aryl or arylalkyl linker and
$R_2$: Any alkyl or aryl group;

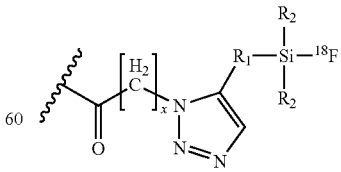

x = 1-5

$R_1$: Any alkyl, aryl or arylalkyl linker and
$R_2$: Any alkyl or aryl group; or -continued
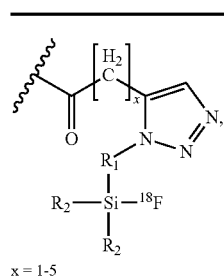
x = 1-5
R₁: Any alkyl, aryl or arylalkyl linker and
R₂: Any alkyl or aryl group.
2. The compound of claim 1 having the structure R'-Linker-R with R'=¹⁸F-Tag and R=Glu-Urea-Lys:
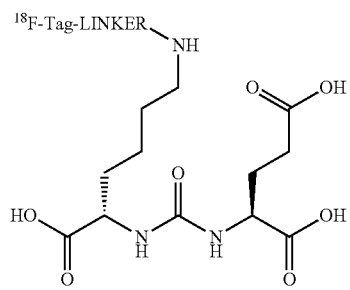
wherein the linker is
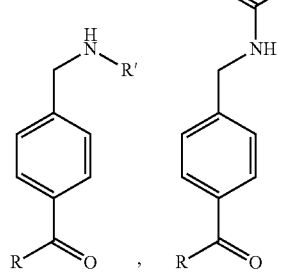
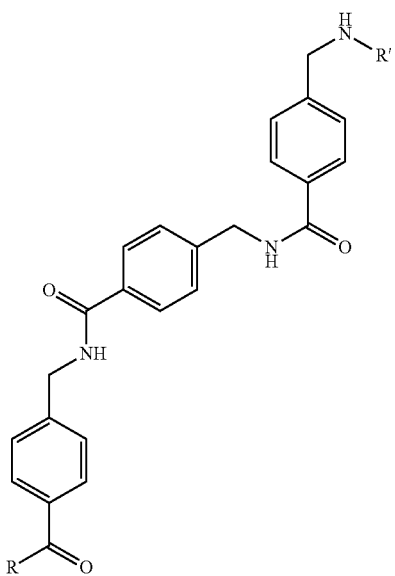
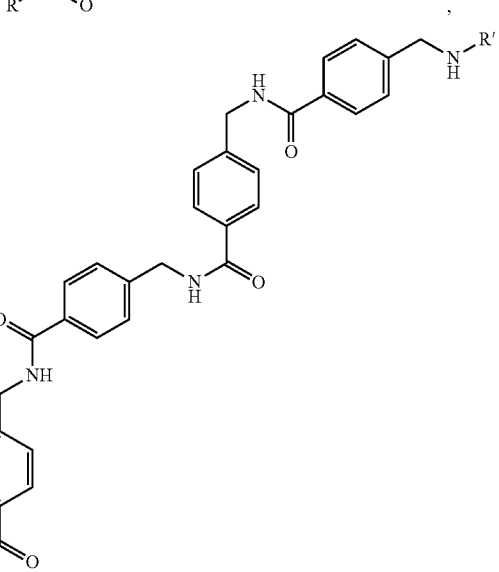
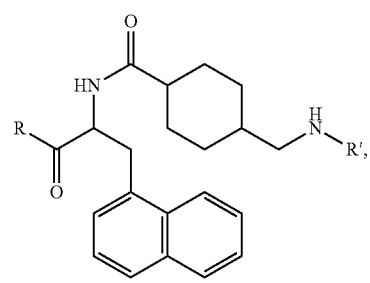
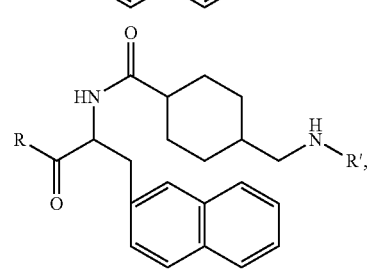

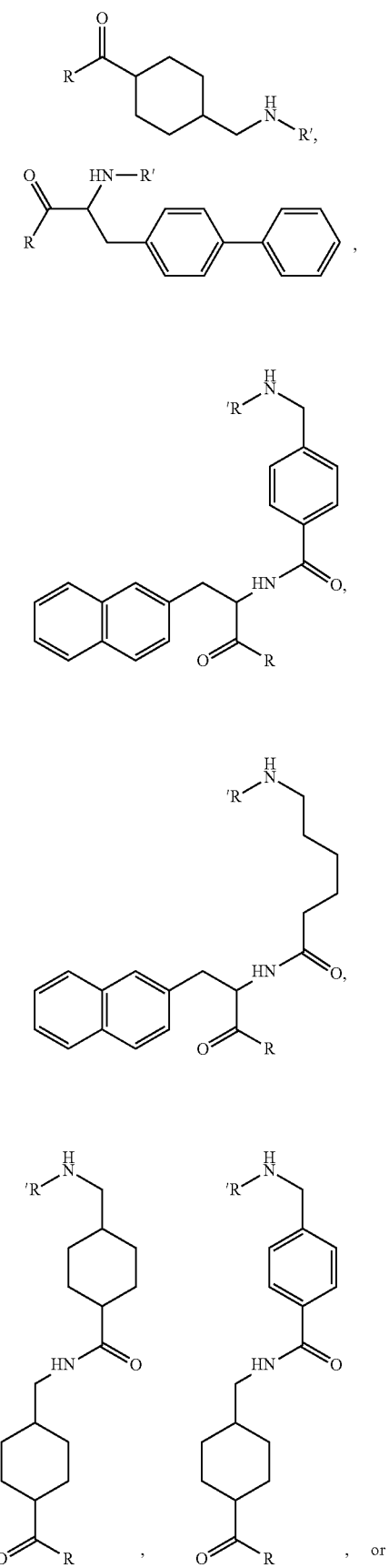
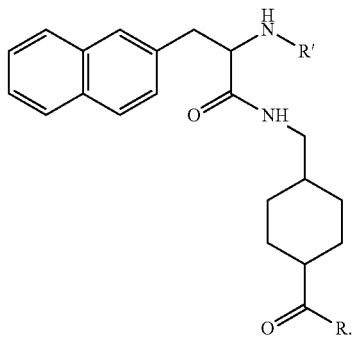
3. The compound of claim 1, wherein the $^{18}$F-Tag is
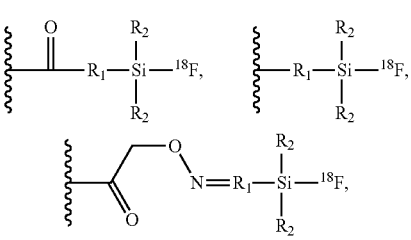
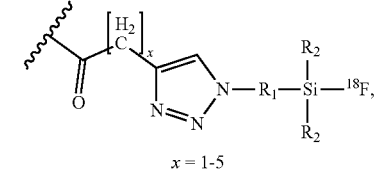
$x = 1\text{-}5$
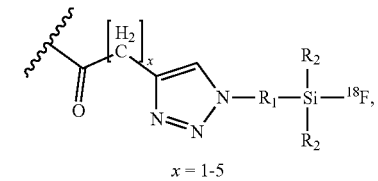
$x = 1\text{-}5$
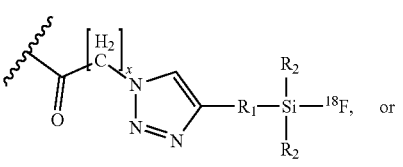
$x = 1\text{-}5$
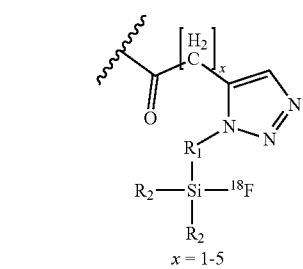
$x = 1\text{-}5$
and $R_1$ is a methyl, 2-ethyl, 3-propyl, 2-,3-,4-phenyl, 2-, 3-,4-phenylmethyl, or 2-,3-,4-phenylpropyl linker.

4. The compound of claim 1, wherein the $^{18}$F-Tag is
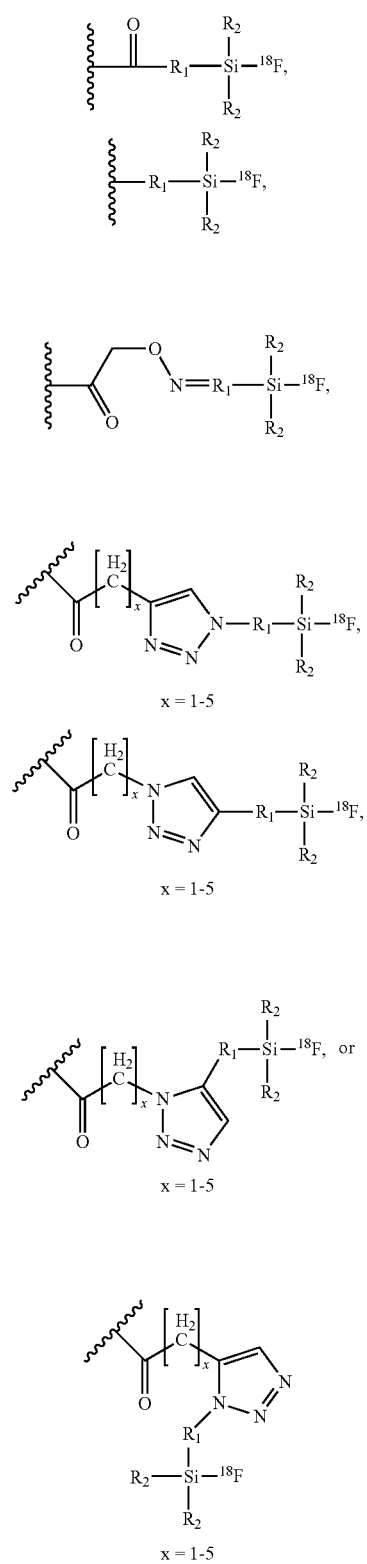
and R$_2$ is methyl, isopropyl, tert-butyl, phenyl or 1-naphtyl.
5. The compound of claim 1, wherein the $^{18}$F-Tag is
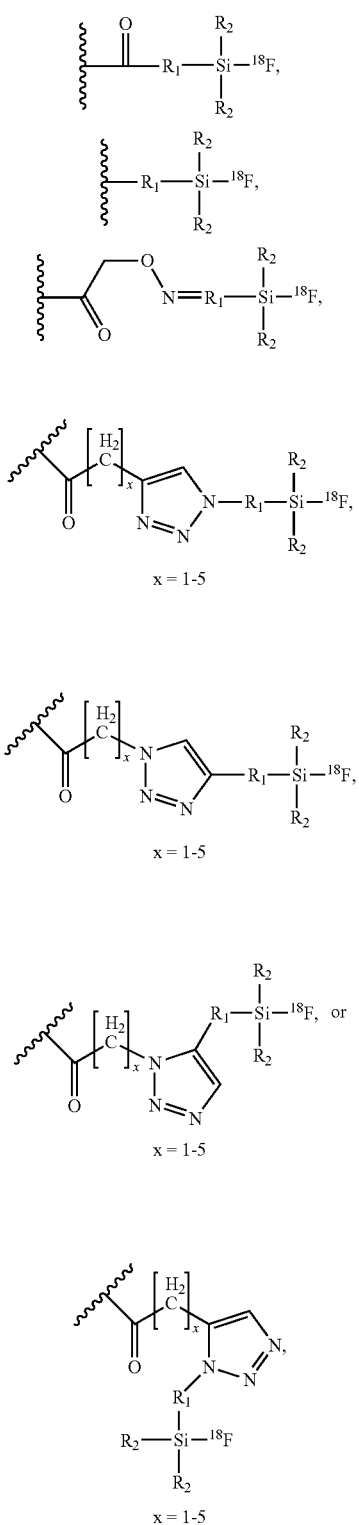
R$_1$ is a methyl, 2-ethyl, 3-propyl, 2-,3-,4-phenyl, 2-,3-,4-phenylmethyl, or 2-,3-,4-phenylpropyl linker and
R$_2$ is methyl, isopropyl, tert-butyl, phenyl or 1-naphtyl.

6. The compound of claim 1, wherein the compound is:
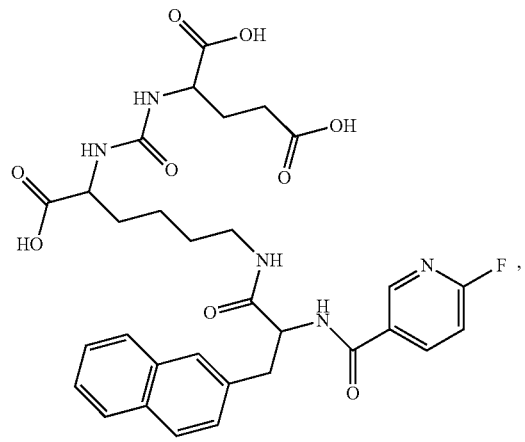 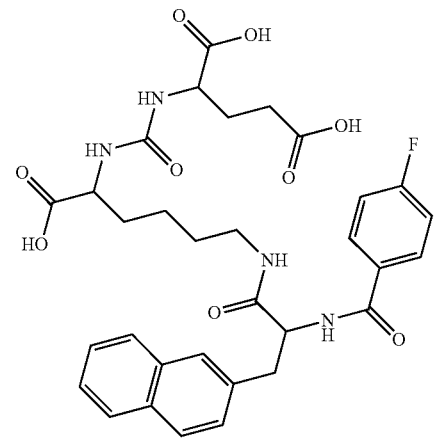
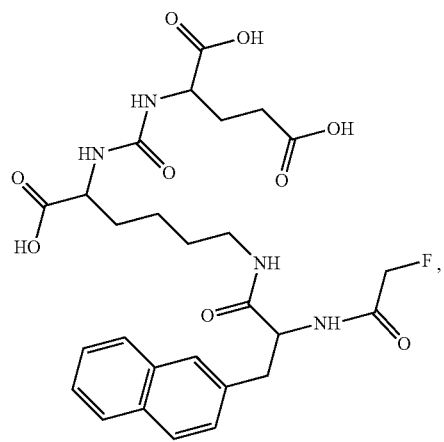 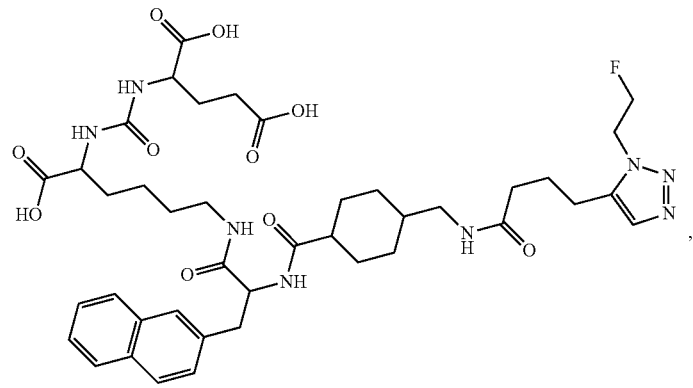
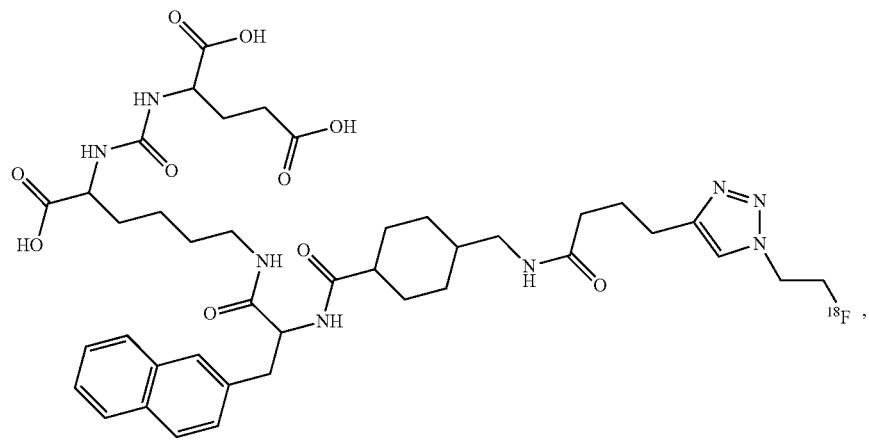

-continued
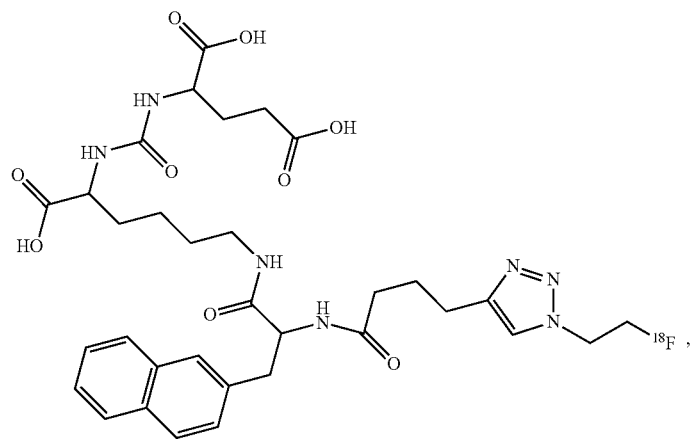
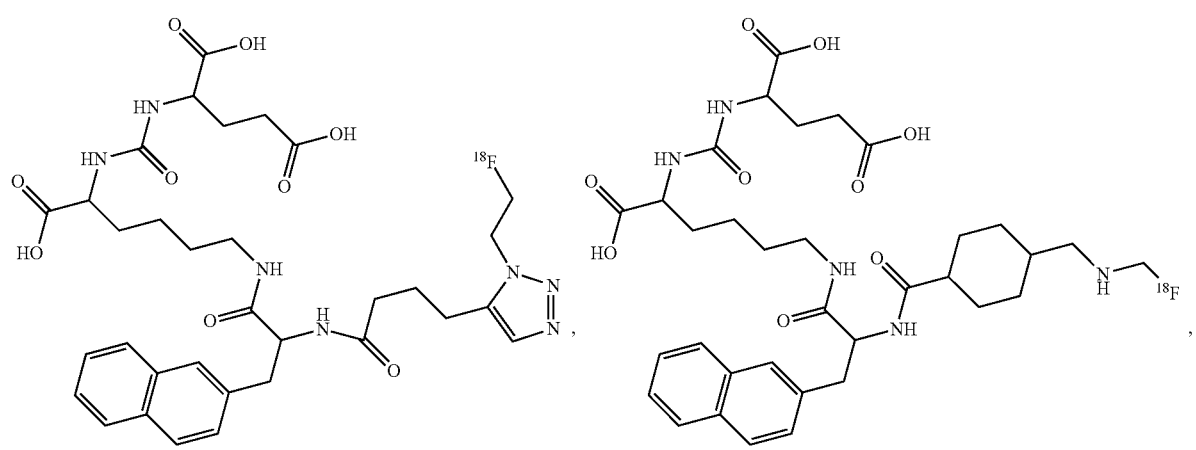
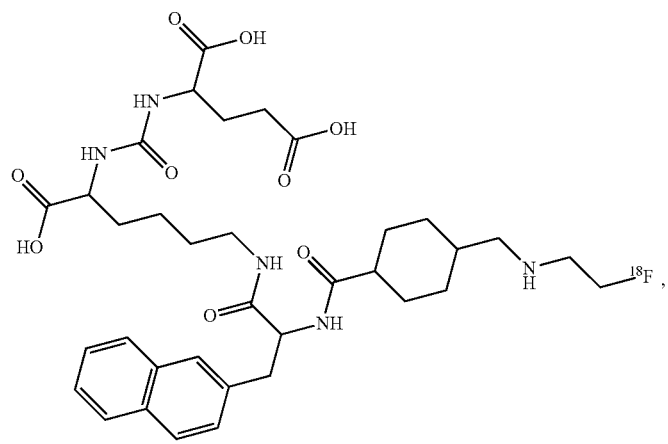

-continued
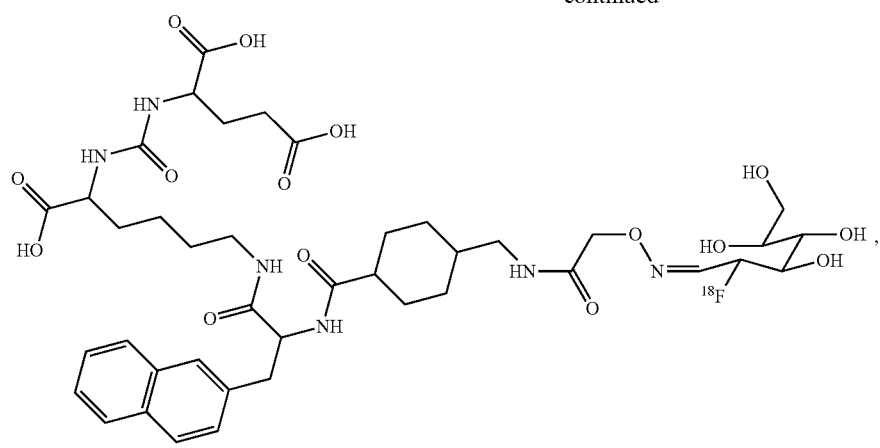
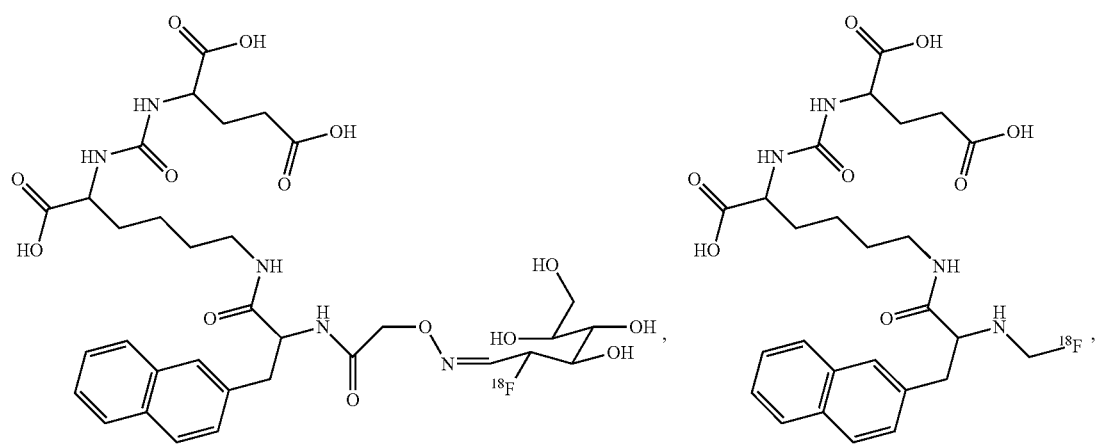
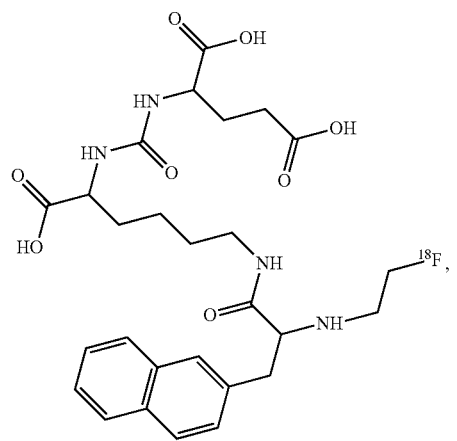

-continued

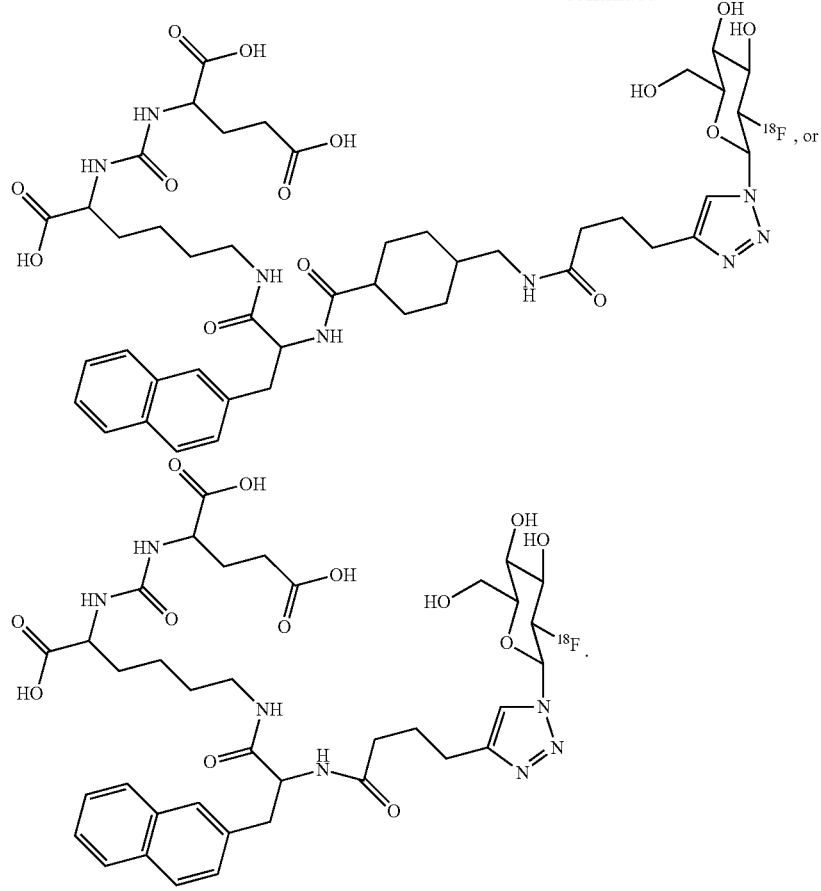

7. A pharmaceutical composition comprising the compound of claim 1, or a pharmaceutically acceptable salt, or ester thereof, and a pharmaceutically acceptable carrier.

8. A pharmaceutical composition comprising the compound of claim 2, or a pharmaceutically acceptable salt, or ester thereof, and a pharmaceutically acceptable carrier.

9. A pharmaceutical composition comprising the compound of claim 6, or a pharmaceutically acceptable salt, or ester thereof, and a pharmaceutically acceptable carrier.

10. A method of imaging in a patient comprising administering the compound of claim 1 to the patient.

11. A method of diagnosing prostate cancer and/or metastasis thereof comprising administering the compound of claim 1.

12. A method of treating prostate cancer and/or metastasis thereof comprising administering the compound of claim 1.

13. A method of imaging in a patient comprising administering the compound of claim 2 to the patient.

14. A method of diagnosing prostate cancer and/or metastasis thereof comprising administering the compound of claim 2.

15. A method of treating prostate cancer and/or metastasis thereof comprising administering the compound of claim 2.

16. A method of imaging in a patient comprising administering the compound of claim 6 to the patient.

17. A method of diagnosing prostate cancer and/or metastasis thereof comprising administering the compound of claim 6.

18. A method of treating prostate cancer and/or metastasis thereof comprising administering the compound of claim 6.

* * * * *

UNITED STATES PATENT AND TRADEMARK OFFICE
CERTIFICATE OF CORRECTION

| | | |
|---|---|---|
| PATENT NO. | : 10,016,519 B2 | Page 1 of 1 |
| APPLICATION NO. | : 15/463059 | |
| DATED | : July 10, 2018 | |
| INVENTOR(S) | : Klaus Kopka et al. | |

It is certified that error appears in the above-identified patent and that said Letters Patent is hereby corrected as shown below:

On the Title Page

(73) Assignees: DEUTSCHES KREBSFORSCHUNGSZENTRIUM should be
DEUTSCHES KREBSFORSCHUNGSZENTRUM Signed and Sealed this
Twenty-third Day of October, 2018

Andrei Iancu
*Director of the United States Patent and Trademark Office*